US008178673B2

(12) United States Patent
Greco et al.

(10) Patent No.: US 8,178,673 B2
(45) Date of Patent: May 15, 2012

(54) PHOSPHONIC ACID COMPOUNDS AS INHIBITORS OF SERINE PROTEASES

(75) Inventors: Michael N. Greco, Lansdale, PA (US); Harold R. Almond, Jr., Maple Glen, PA (US); Michael J. Hawkins, Ambler, PA (US); Eugene Powell, Pipersville, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 199 days.

(21) Appl. No.: 12/288,941

(22) Filed: Oct. 24, 2008

(65) Prior Publication Data

US 2009/0118508 A1      May 7, 2009

Related U.S. Application Data

(60) Division of application No. 10/414,782, filed on Apr. 16, 2003, now Pat. No. 7,459,461, which is a continuation-in-part of application No. 10/273,208, filed on Oct. 17, 2002, now abandoned.

(60) Provisional application No. 60/330,343, filed on Oct. 19, 2001.

(51) Int. Cl.
*C07F 9/28* (2006.01)
*C07F 9/38* (2006.01)
*C07F 9/572* (2006.01)
*C07F 9/59* (2006.01)
*C07F 9/6509* (2006.01)
*C07F 9/655* (2006.01)
*C07F 9/6558* (2006.01)
*C07F 9/6561* (2006.01)

(52) U.S. Cl. .................................. 544/337; 546/22
(58) Field of Classification Search ................ None
See application file for complete search history.

(56) References Cited

U.S. PATENT DOCUMENTS

| 4,511,551 | A | 4/1985 | Cardarelli et al. |
| 4,704,382 | A | 11/1987 | Fowler et al. |
| 4,822,780 | A | 4/1989 | Tsuda et al. |
| 5,508,273 | A | 4/1996 | Beers et al. |
| 6,080,738 | A | 6/2000 | Akahoshi et al. |
| 6,528,514 | B1 | 3/2003 | Kobayashi et al. |
| 7,459,461 | B2 | 12/2008 | Greco et al. |
| 2009/0118235 | A1 | 5/2009 | Greco et al. |
| 2009/0118504 | A1 | 5/2009 | Greco et al. |
| 2009/0118508 | A1 | 5/2009 | Greco et al. |
| 2009/0124581 | A1 | 5/2009 | Greco et al. |
| 2009/0131671 | A1 | 5/2009 | Greco et al. |
| 2009/0137528 | A1 | 5/2009 | Greco et al. |
| 2009/0143396 | A1 | 6/2009 | Malecha et al. |
| 2011/0086819 | A1 | 4/2011 | Greco et al. |
| 2011/0092457 | A1 | 4/2011 | Greco et al. |
| 2011/0092705 | A1 | 4/2011 | Greco et al. |

FOREIGN PATENT DOCUMENTS

| BE | 633914 | 12/1963 |
| WO | 97/03679 A1 | 2/1997 |
| WO | WO 03/035654 | 5/2003 |

OTHER PUBLICATIONS

Robert V. Hoffman, Organic Chemistry: An Intermediate Text; Chapter 6. Stereochemical and Conformational Isomerism, 2nd Ed., John Wiley & Sons, Inc., 124-182 (2004).*
DeGaravilla et al "A Novel, Potent Dual Inhibitor of the Leukocyte Proteases Cathepsin G and Chymase," TheJournal of Biological Chemistry, 2005, 18001-18007. 280 (18).
DeBoer, Willem, "Perspectives for cytokine antagonist therapy in COPD," Drug Discovery Today, 2005, 93-106, 10 (2).
Barnes, Peter J., "New Treaments for COPD," Nature Reviews, 2002, 437-446, 1.
Henning et al, "Synthesis and Neuroleptic Activity of a Series of 1-[1-(Benzo-1,4-dioxan-2-ylmethyl)-4piperidinyl] benzimidazoline Derivatives," Journal of Medicianl Chemistry, 1987, 814-819, 30.
Yao, Yu-Lin, "Association between the Expression of Mast Cell Chymase and Intraperitoneal Adhesion Formation in Mice," Journal of Surgical Research, 2000, 4-44, 92.
Sands, Howard et al, LEX 032, "A novel recombinant human protein for the treatment of ischaemic reperfusion injury," Exp Opin. Invest Drugs, 1999, 1907-1916, 8:11.
Akahoshi, Fumihiko et al, "Synthesis, Structure-Activity Relationships and Pharmacokineic Profiles of Nonpeptide Difluoromethylene Ketones as Novel Inhibitors of Human Chymase," J. Med. Chem., 2001, 1297-1304, 44.
Abraham, W., "Pharmacology of Allergen-Induced Early and Late Airway Responses and Antigen-Induced Airway Hyperresonsiveness in Allergic Sheep", Pulmonary Pharmacology, pp. 33-43 (1989).
Ahn, H-S., et al. "Development of Proteinase-Activated Receptor 1 Antagonists as Therapeutic Agents for Thrombosis, Restenosis and Inflammatory Diseases", Current Pharmaceutical Design, vol. 9, pp. 2349-2365 (2003).
Berge, S., et al. "Pharmaceutical Salts", Journal of Pharmaceutical Sciences, vol. 66, No. 1, pp. 1-19 (1977).
Chambers, R., et al. "Leukotriene Antagonists: Patent Highlights 1996-1998", Expert Opinion Therapeutic Patents, vol. 9(1) pp. 19-26 (1999).
De Lombaert, S., et al. "N-Phosphon Methyl Dipeptides and Their Phosphonate Pr drugs, a New Generation of Neutral Endopeptidase (NEP, EC 3.4.24-11 Inhibit rs[1]", J. Medical Chemistry, vol. 37, pp. 498-511 (1994). De Lombaert, S., et al. "Non-Peptidic Inhibitors of Neutral Endopeptidase 24.11 2. Design and Pharmacology of Orally Active Phosphonate Prodrugs", Bioorganic & Medicinal Chemistry Letters, vol. 5, No. 2, pp. 151-154 (1995).
Deprele, S., et al. "Palladium-Catalyzed Hydrophosphinylation of Alk nes and Alkynes", JACCS, vol. 124, pp. 9386-9387 (2002).
Dorwald, F., "Side Reaction sin Organic Synthesis", Wiley, VCH, Weinheim, pp. 1X of Preface (2005).
Gould, P., "Salt Selection of Basic Drugs", International Journal of Pharmaceutics, vol. 33 pp. 201-217 (1986).
Greco, M., et al. Nonpeptide Inhibitors of Cathepsin G: Optimization of a Novel β-Ketophosphonic Acid Lead by Structure-Based Drug Design, J. American Chemical Society, vol. 124 p. 3810-3811 (2002).
Katritzky, A., et al. "A One-Pot Procedure for the Preparation of Phosphonic Acids from Alkyl Halides", Organic Preparations and Procedure Int. vol. 22(2), pp. 209-213 (1990.

(Continued)

*Primary Examiner* — Janet Andres
*Assistant Examiner* — Timothy R Rozof
(74) *Attorney, Agent, or Firm* — Yuriy P. Stercho

(57) ABSTRACT

The present invention is directed to phosphonic acid compounds useful as serine protease inhibitors, compositions thereof and methods for treating inflammatory and serine protease mediated disorders.

9 Claims, 2 Drawing Sheets

OTHER PUBLICATIONS

Numerof, R., et al. "Pulmonary-Allergy, Dermatological, Gastrointestinal & Arthritis", Expert Opinion Investigational Drugs, vol. 6(7), pp. 811-817 (1997).

Schwender, C., et al. "1-Naphthylmethylphosphonic Acid Derivatives as Osteoclastic Acid Phosphateas Inhibitors", Bioorganic & Medical Chemistry Letters, vol. 5, No. 16, pp. 1801-1806 (1995).

Schoofs, L., et al. "Trypsin and Chymotrypsin Inhibitors in Insects and Gut Leeches", Current Pharmaceutical Design, vol. 8, pp. 483-491 (2002).

Steininger, E., "The Preparation of Bis-phosphinic Acid Esters and Other Bis Phosphorus Compounds", English Abstract.

Caplus: 2002-11331 "Elastase Inhibitors".

Caplus: 1997-171939 "Structure and Function of Thrombin Receptor".

International Search Report for corresponding Application No. PCT/US02/33206, mailed Mar. 14, 2003.

International Search Report for corresponding Application No. PCT/US04/011490, mailed Jan. 7, 2005.

International Search Report for corresponding Application No. PCT/US02/33206, mailed Aug. 8, 2003.

* cited by examiner

PHOSPHONIC ACID COMPOUNDS AS INHIBITORS OF SERINE PROTEASES

CROSS REFERENCE TO RELATED APPLICATIONS

This application is a divisional of U.S. Ser. No. 10/414,782, filed Apr. 16, 2003 now U.S. Pat. No. 7,459,461, which is a continuation-in-part of U.S. Ser. No. 10/273,208, filed Oct. 17, 2002, now abandoned, which claims benefit of provisional application Ser. No. 60/330,343, filed Oct. 19, 2001, which are incorporated herein by reference.

FIELD OF THE INVENTION

The present invention relates to certain novel compounds, methods for preparing the compounds, compositions, intermediates and derivatives thereof and for treating inflammatory and serine protease mediated disorders. More particularly, the phosphonic acid compounds of the present invention are serine protease inhibitors useful for treating inflammatory and serine protease mediated disorders.

BACKGROUND OF THE INVENTION

Serine proteases represent a broad class of endopeptidases that are involved in physiological processes such as blood coagulation, complement activation, phagocytosis and turnover of damaged cell tissue. For example, cathepsin G (cat G) is a chymotrypsin-like serine protease found in the azurophilic granules of polymorphonuclear leukocytes. Along with other serine proteases such as human neutrophil elastase and protease 3, cat G functions to degrade proteins during inflammatory responses. Cat G is thought to degrade human elastin during chronic lung inflammation, a process which may in part be responsible for asthma, pulmonary emphysema, chronic obstructive pulmonary diseases (COPD) as well as other pulmonary inflammatory conditions. Similarly, human chymase (HC) is a chymotrypsin-like serine protease synthesized in mast cells. HC has a variety of functions, including degradation of extracellular matrix proteins, cleavage of angiotensin I to angiotensin II and activation of matrix proteases and cytokines. Inadequate control by their natural inhibitors can cause these enzymes to degrade healthy constituents of the extracellular matrix, and thereby contribute to inflammatory disorders such as asthma, emphysema, bronchitis, psoriasis, allergic rhinitis, viral rhinitis, ischemia, arthritis and reperfusion injury. Thus, small molecule inhibitors of cat G and HC are likely to represent useful therapeutic agents.

U.S. Pat. No. 5,508,273 to Beers, et al. and *Bioorganic & Med. Chem. Lett.*, 1995, 5, (16), 1801-1806 describe phosphonic acid compounds useful in treating bone wasting diseases. In particular, 1-napthylmethylphosphonic acid derivatives have been described as osteoclastic acid phosphatase inhibitors of the formula:

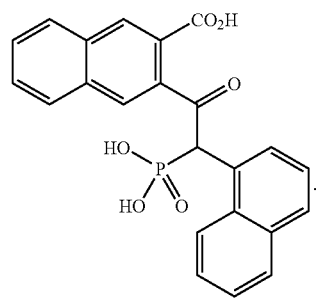

Accordingly, it is an object of the present invention to provide phosphonic acid compounds that are serine protease inhibitors (in particular, inhibitors of cathepsin G and chymase) useful for treating inflammatory and serine protease mediated disorders. It is another object of the invention to provide a process for preparing phosphonic or phosphinic acid compounds, compositions, intermediates and derivatives thereof. It is a further object of the invention to provide methods for treating inflammatory and serine protease mediated disorders.

SUMMARY OF THE INVENTION

This invention is directed to compounds of Formula (I):

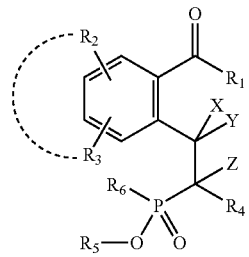

Formula (I)

wherein
$R_1$ is selected from the group consisting of a heterocyclyl ring (wherein the point of attachment for the heterocyclyl ring at $R_1$ is a nitrogen ring atom) and —$N(R_7R_8)$; wherein the heterocyclyl ring is optionally substituted with one to two substituents independently selected from the group consisting of:
a). $C_{1-8}$ alkyl optionally substituted on a terminal carbon atom with a substituent selected from the group consisting of aryl, heteroaryl, (halo)$_{1-3}$ and hydroxy;
b). $C_{1-8}$ alkoxy optionally substituted on a terminal carbon atom with a substituent selected from the group consisting of carboxyl, (halo)$_{1-3}$ and hydroxy;
c). aryl;
d). heteroaryl;
e). cyano;
f). halogen;
g). hydroxy;
h). nitro; and,
i). heterocyclyl optionally substituted with one to two substituents independently selected from the group consisting of oxo and aryl; and, optionally fused with the carbon of attachment to form a spiro heterocyclyl moiety;
and, wherein the aryl portion of the a). and i). substituent, the heteroaryl portion of the a). substituent and the c). aryl and d). heteroaryl substituents are optionally substituted with one to four substituents independently selected from the group consisting of $C_{1-4}$ alkyl, $C_{2-4}$ alkenyl, $C_{1-4}$ alkoxy, cycloalkyl, heterocyclyl, aryl, aryl($C_{1-4}$)alkyl, aryloxy, heteroaryl, heteroaryl($C_{1-4}$)alkyl, halogen, hydroxy, nitro, $(halo)_{1-3}(C_{1-4})$alkyl and $(halo)_{1-3}(C_{1-4})$alkoxy;

$R_7$ is selected from the group consisting of hydrogen, $C_{1-8}$ alkyl and $C_{2-8}$ alkenyl;

$R_8$ is selected from the group consisting of:

aa). $C_{1-8}$ alkyl optionally substituted on a terminal carbon atom with a substituent selected from the group consisting of cycloalkyl, heterocyclyl, aryl, heteroaryl, amino (with two substituents independently selected from the group consisting of hydrogen and $C_{1-8}$ alkyl), $(halo)_{1-3}$ and hydroxy;

ab). cycloalkyl;

ac). cycloalkenyl; and, ad). heterocyclyl (wherein the point of attachment at $R_8$ is a carbon ring atom);

wherein the ab). cycloalkyl, ac). cycloalkenyl and ad). heterocyclyl (wherein the ad). heterocyclyl contains at least one nitrogen ring atom) substituents and the cycloalkyl, heterocyclyl, aryl and heteroaryl portions of the aa). substituent are optionally substituted with one to four substituents independently selected from the group consisting of:

ba). $C_{1-8}$ alkyl optionally substituted on a terminal carbon atom with a substituent selected from the group consisting of amino (with two substituents independently selected from the group consisting of hydrogen and $C_{1-8}$ alkyl), $(halo)_{1-3}$ and hydroxy;

bb). $C_{1-8}$ alkoxy optionally substituted on a terminal carbon atom with a substituent selected from the group consisting of carboxyl, $(halo)_{1-3}$ and hydroxy;

bc). carbonyl substituted with a substituent selected from the group consisting of $C_{1-8}$ alkyl, aryl, aryl($C_{1-8}$)alkyl, aryl($C_{2-8}$)alkenyl, heteroaryl, heteroaryl($C_{1-8}$)alkyl and heteroaryl($C_{2-8}$)alkenyl;

bd). aryl;

be). heteroaryl;

bf). amino substituted with two substituents independently selected from the group consisting of hydrogen and $C_{1-8}$ alkyl;

bg). cyano;

bh). halogen;

bi). hydroxy;

bj). nitro;

bk). heterocyclyl optionally substituted with one to two oxo substituents; and, bl). sulfonyl substituted with a substituent selected from the group consisting of $C_{1-8}$ alkyl, aryl, aryl($C_{1-8}$)alkyl, aryl($C_{2-8}$)alkenyl, heteroaryl, heteroaryl($C_{1-8}$)alkyl and heteroaryl($C_{2-8}$)alkenyl;

wherein the bd). aryl, be). heteroaryl and bk). heterocyclyl substituents and the aryl and heteroaryl portions of the bc). substituent are optionally substituted with one to four substituents independently selected from the group consisting of $C_{1-4}$ alkyl (optionally substituted on a terminal carbon atom with a substituent selected from the group consisting of amino (substituted with two substituents independently selected from the group consisting of hydrogen and $C_{1-8}$ alkyl), $(halo)_{1-3}$ and hydroxy), $C_{1-4}$ alkoxy (optionally substituted on a terminal carbon atom with a substituent selected from the group consisting of $(halo)_{1-3}$), amino (substituted with two substituents independently selected from the group consisting of hydrogen and $C_{1-4}$ alkyl), halogen, hydroxy and nitro;

and, provided that the optional substituent attached to the ad). heterocyclyl nitrogen ring atom is not selected from the group consisting of bf). amino (substituted with two substituents independently selected from the group consisting of hydrogen and $C_{1-8}$ alkyl), bh). halogen, bi). hydroxy and bj). nitro;

$R_4$ is selected from the group consisting of $C_{1-4}$ alkyl (optionally substituted on a terminal carbon atom with a substituent selected from the group consisting of aryl and heteroaryl), aryl and heteroaryl; wherein aryl and heteroaryl and the aryl and heteroaryl portions of the substituted alkyl are optionally substituted with one to four substituents independently selected from the group consisting of $C_{1-4}$ alkyl, amino (substituted with two substituents independently selected from the group consisting of hydrogen and $C_{1-4}$ alkyl), cyano, halogen, hydroxy and $(halo)_{1-3}(C_{1-8})$alkyl;

$R_2$ and $R_3$ are attached to a benzene ring and independently selected from the group consisting of ca). hydrogen;

cb). $C_{1-4}$ alkyl optionally substituted on a terminal carbon atom with a substituent selected from the group consisting of amino (substituted with two substituents independently selected from the group consisting of hydrogen and $C_{1-4}$ alkyl), $(halo)_{1-3}$ and hydroxy;

cc). $C_{1-4}$ alkoxy optionally substituted on a terminal carbon atom with a substituent selected from the group consisting of $(halo)_{1-3}$ and hydroxy;

cd). $C_{2-4}$ alkenyl;

ce). amino substituted with two substituents independently selected from the group consisting of hydrogen and $C_{1-4}$ alkyl;

cf). halogen; and, cg). hydroxy;

optionally, $R_2$ and $R_3$ together form at least one ring fused to the benzene ring; thereby providing a multiple ring system; wherein the multiple ring system is selected from the group consisting of $C_9$-$C_{14}$ benzo fused cycloalkyl, $C_9$-$C_{14}$ benzo fused cycloalkenyl, $C_9$-$C_{14}$ benzo fused aryl, benzo fused heterocyclyl and benzo fused heteroaryl; and, wherein the multiple ring system can optionally be substituted with one to four substituents independently selected from the group consisting of da). $C_{1-4}$ alkyl optionally substituted on a terminal carbon atom with a substituent selected from the group consisting of amino (substituted with two substituents independently selected from the group consisting of hydrogen and $C_{1-4}$ alkyl), $(halo)_{1-3}$ and hydroxy;

db). $C_{1-4}$ alkoxy optionally substituted on a terminal carbon atom with a substituent selected from the group consisting of $(halo)_{1-3}$ and hydroxy;

dc). amino substituted with two substituents independently selected from the group consisting of hydrogen and $C_{1-4}$ alkyl;

dd). halogen;

de). hydroxy; and, df). nitro;

$R_5$ is selected from the group consisting of hydrogen and $C_{1-8}$ alkyl (optionally substituted on a terminal carbon atom with a substituent selected from the group consisting of amino (substituted with two substituents independently selected from the group consisting of hydrogen and $C_{1-4}$ alkyl), $(halo)_{1-3}$ and hydroxy) and aryl (optionally substituted with one to four substituents independently selected from the group consisting of $C_{1-8}$ alkyl and halogen);

$R_6$ is selected from the group consisting of $C_{1-8}$ alkyl, aryl $(C_{1-8})$alkyl, $C_{1-8}$ alkoxy, aryl$(C_{1-8})$alkoxy, $C_{2-8}$ alkenyl, $C_{2-8}$ alkenyloxy, aryl$(C_{2-8})$alkenyl, aryl$(C_{2-8})$alkenyloxy, aryl, aryloxy and hydroxy;

X and Y are independently selected from the group consisting of hydrogen, $C_{1-8}$ alkyl (optionally substituted on a terminal carbon atom with a substituent selected from the group consisting of cycloalkyl, heterocyclyl, aryl, heteroaryl, amino (substituted with two substituents independently selected from the group consisting of hydrogen and $C_{1-8}$ alkyl), (halo)$_{1-3}$ and hydroxy), $C_{1-8}$ alkoxy (optionally substituted on a terminal carbon atom with a substituent selected from the group consisting of aryl, (halo)$_{1-3}$ and hydroxy), $C_{2-8}$ alkenyloxy, cycloalkyl, heterocyclyl, aryl, aryloxy, heteroaryl and hydroxy; optionally, X and Y are fused together with the carbon of attachment to form a spiro cycloalkyl or heterocyclyl moiety; and, optionally, Y is not present; wherein X is one substituent attached by a double-bond selected from the group consisting of O, S, imino, $(C_{1-4})$alkylimino and hydroxyimino; and, Z is selected from the group consisting of a bond, hydrogen and $C_{1-8}$ alkyl; if Z is a bond (wherein Z forms a double bond with the carbon of attachment for X), then Y is not present and X is one substituent attached by a single-bond selected from the group consisting of hydrogen, $C_{1-8}$ alkoxy, $C_{2-8}$ alkenyloxy, aryloxy, aryl$(C_{1-4})$alkoxy and hydroxy, and isomers, racemates, enantiomers, diastereomers and salts thereof.

Embodiments of the present invention include a process for preparing a compound of Formula (I) comprising coupling under suitable conditions a first compound of Formula (A):

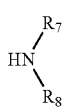

Formula (A)

with a second compound selected from the group consisting of Formula (B) and Formula (C):

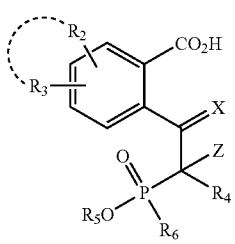

Formula (B)

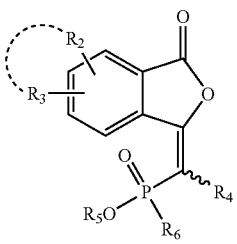

Formula (C)

to produce a third compound selected from the group consisting of Formula (D) and Formula (E):

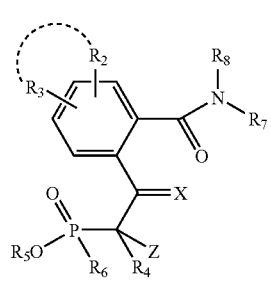

Formula (D)

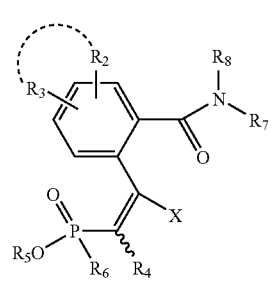

Formula (E)

wherein $R_7$ is selected from the group consisting of hydrogen, $C_{1-8}$ alkyl and $C_{2-8}$ alkenyl;

$R_8$ is selected from the group consisting of:

aa). $C_{1-8}$ alkyl optionally substituted on a terminal carbon atom with a substituent selected from the group consisting of cycloalkyl, heterocyclyl, aryl, heteroaryl, amino (substituted with two substituents independently selected from the group consisting of hydrogen and $C_{1-8}$ alkyl), (halo)$_{1-3}$ and hydroxy;

ab). cycloalkyl;

ac). cycloalkenyl; and, ad). heterocyclyl (wherein the point of attachment at $R_8$ is a carbon ring atom);

wherein the ab). cycloalkyl, ac). cycloalkenyl and ad). heterocyclyl (wherein the ad). heterocyclyl contains at least one nitrogen ring atom) substituents and the cycloalkyl, heterocyclyl, aryl and heteroaryl portions of the aa). substituent are optionally substituted with one to four substituents independently selected from the group consisting of:

ba). $C_{1-8}$ alkyl optionally substituted on a terminal carbon atom with a substituent selected from the group consisting of amino (with two substituents independently selected from the group consisting of hydrogen and $C_{1-8}$ alkyl), (halo)$_{1-3}$ and hydroxy;

bb). $C_{1-8}$ alkoxy optionally substituted on a terminal carbon atom with a substituent selected from the group consisting of carboxyl, (halo)$_{1-3}$ and hydroxy;

bc). carbonyl substituted with a substituent selected from the group consisting of $C_{1-8}$ alkyl, aryl, aryl$(C_{1-8})$alkyl, aryl$(C_{2-8})$alkenyl, heteroaryl, heteroaryl$(C_{1-8})$alkyl and heteroaryl$(C_{2-8})$alkenyl;

bd). aryl;

be). heteroaryl;

bf). amino substituted with two substituents independently selected from the group consisting of hydrogen and $C_{1-8}$ alkyl;

bg). cyano;

bh). halogen;

bi). hydroxy;

bj). nitro;

bk). heterocyclyl optionally substituted with one to two oxo substituents; and, b1). sulfonyl substituted with a substituent selected from the group consisting of $C_{1-8}$ alkyl, aryl, aryl($C_{1-8}$)alkyl, aryl ($C_{2-8}$)alkenyl, heteroaryl, heteroaryl($C_{1-8}$)alkyl and heteroaryl($C_{2-8}$)alkenyl;

wherein the bd). aryl, be). heteroaryl and bk). heterocyclyl substituents and the aryl and heteroaryl portions of the bc). substituent are optionally substituted with one to four substituents independently selected from the group consisting of $C_{1-4}$ alkyl (optionally substituted on a terminal carbon atom with a substituent selected from the group consisting of amino (substituted with two substituents independently selected from the group consisting of hydrogen and $C_{1-8}$ alkyl), (halo)$_{1-3}$ and hydroxy), $C_{1-4}$ alkoxy (optionally substituted on a terminal carbon atom with a substituent selected from the group consisting of (halo)$_{1-3}$), amino (substituted with two substituents independently selected from the group consisting of hydrogen and $C_{1-4}$ alkyl), halogen, hydroxy and nitro;

and, provided that the optional substituent attached to the ad). heterocyclyl nitrogen ring atom is not selected from the group consisting of bf). amino (substituted with two substituents independently selected from the group consisting of hydrogen and $C_{1-8}$ alkyl), bh). halogen, bi). hydroxy and bj). nitro;

$R_4$ is selected from the group consisting of $C_{1-4}$ alkyl (optionally substituted on a terminal carbon atom with a substituent selected from the group consisting of aryl and heteroaryl), aryl and heteroaryl; wherein aryl and heteroaryl and the aryl and heteroaryl portions of the substituted alkyl are optionally substituted with one to four substituents independently selected from the group consisting of $C_{1-4}$ alkyl, amino (substituted with two substituents independently selected from the group consisting of hydrogen and $C_{1-4}$ alkyl), cyano, halogen, hydroxy and (halo)$_{1-3}$($C_{1-8}$) alkyl;

$R_2$ and $R_3$ are attached to a benzene ring and independently selected from the group consisting of
ca). hydrogen;
cb). $C_{1-4}$ alkyl optionally substituted on a terminal carbon atom with a substituent selected from the group consisting of amino (substituted with two substituents independently selected from the group consisting of hydrogen and $C_{1-4}$ alkyl), (halo)$_{1-3}$ and hydroxy;
cc). $C_{1-4}$ alkoxy optionally substituted on a terminal carbon atom with a substituent selected from the group consisting of (halo)$_{1-3}$ and hydroxy;
cd). $C_{2-4}$ alkenyl;
ce). amino substituted with two substituents independently selected from the group consisting of hydrogen and $C_{1-4}$ alkyl;
cf). halogen; and,
cg). hydroxy;
optionally, $R_2$ and $R_3$ together form at least one ring fused to the benzene ring; thereby providing a multiple ring system; wherein the multiple ring system is selected from the group consisting of $C_9$-$C_{14}$ benzo fused cycloalkyl, $C_9$-$C_{14}$ benzo fused cycloalkenyl, $C_9$-$C_{14}$ benzo fused aryl, benzo fused heterocyclyl and benzo fused heteroaryl; and, wherein the multiple ring system can optionally be substituted with one to four substituents independently selected from the group consisting of:
da). $C_{1-4}$ alkyl optionally substituted on a terminal carbon atom with a substituent selected from the group consisting of amino (substituted with two substituents independently selected from the group consisting of hydrogen and $C_{1-4}$ alkyl), (halo)$_{1-3}$ and hydroxy;
db). $C_{1-4}$ alkoxy optionally substituted on a terminal carbon atom with a substituent selected from the group consisting of (halo)$_{1-3}$ and hydroxy;
dc). amino substituted with two substituents independently selected from the group consisting of hydrogen and $C_{1-4}$ alkyl;
dd). halogen;
de). hydroxy; and,
df). nitro;

$R_5$ is selected from the group consisting of hydrogen and $C_{1-8}$ alkyl (optionally substituted on a terminal carbon atom with a substituent selected from the group consisting of amino (substituted with two substituents independently selected from the group consisting of hydrogen and $C_{1-4}$ alkyl), (halo)$_{1-3}$ and hydroxy) and aryl (optionally substituted with one to four substituents independently selected from the group consisting of $C_{1-8}$ alkyl and halogen);

$R_6$ is selected from the group consisting of $C_{1-8}$ alkyl, aryl ($C_{1-8}$)alkyl, $C_{1-8}$ alkoxy, aryl($C_{1-8}$)alkoxy, $C_{2-8}$ alkenyl, $C_{2-8}$ alkenyloxy, aryl($C_{2-8}$)alkenyl, aryl($C_{2-8}$)alkenyloxy, aryl, aryloxy and hydroxy;

X is selected from the group consisting of O, S, imino, ($C_{1-4}$)alkylimino and hydroxyimino; and, Z is selected from the group consisting of a bond, hydrogen and $C_{1-8}$ alkyl; if Z is a bond (wherein Z forms a double bond with the carbon of attachment for X), then X is selected from the group consisting of hydrogen, $C_{1-8}$ alkoxy, $C_{2-8}$ alkenyloxy, aryloxy, aryl($C_{1-4}$)alkoxy and hydroxy, and isomers, racemates, enantiomers, diastereomers and salts thereof.

Embodiments of the present invention include a compound of Formula (C):

Formula (C)

wherein $R_2$ and $R_3$ are attached to a benzene ring and independently selected from the group consisting of
ca). hydrogen;
cb). $C_{1-4}$ alkyl optionally substituted on a terminal carbon atom with a substituent selected from the group consisting of amino (substituted with two substituents independently selected from the group consisting of hydrogen and $C_{1-4}$ alkyl), (halo)$_{1-3}$ and hydroxy;
cc). $C_{1-4}$ alkoxy optionally substituted on a terminal carbon atom with a substituent selected from the group consisting of (halo)$_{1-3}$ and hydroxy;
cd). $C_{2-4}$ alkenyl;
ce). amino substituted with two substituents independently selected from the group consisting of hydrogen and $C_{1-4}$ alkyl;
cf). halogen; and,
cg). hydroxy;
optionally, $R_2$ and $R_3$ together form at least one ring fused to the benzene ring; thereby providing a multiple ring system; wherein the multiple ring system is selected from the group consisting of C$_9$-C$_{14}$ benzo fused cycloalkyl, C$_9$-C$_{14}$ benzo fused cycloalkenyl, C$_9$-C$_{14}$ benzo fused aryl, benzo fused heterocyclyl and benzo fused heteroaryl; and, wherein the multiple ring system can optionally be substituted with one to four substituents independently selected from the group consisting of da). C$_{1-4}$ alkyl optionally substituted on a terminal carbon atom with a substituent selected from the group consisting of amino (substituted with two substituents independently selected from the group consisting of hydrogen and C$_{1-4}$ alkyl), (halo)$_{1-3}$ and hydroxy;

db). C$_{1-4}$ alkoxy optionally substituted on a terminal carbon atom with a substituent selected from the group consisting of (halo)$_{1-3}$ and hydroxy;

dc). amino substituted with two substituents independently selected from the group consisting of hydrogen and C$_{1-4}$ alkyl;

dd). halogen;

de). hydroxy; and, df). nitro;

R$_4$ is selected from the group consisting of C$_{1-4}$ alkyl (optionally substituted on a terminal carbon atom with a substituent selected from the group consisting of aryl and heteroaryl), aryl and heteroaryl; wherein aryl and heteroaryl and the aryl and heteroaryl portions of the substituted alkyl are optionally substituted with one to four substituents independently selected from the group consisting of C$_{1-4}$ alkyl, amino (substituted with two substituents independently selected from the group consisting of hydrogen and C$_{1-4}$ alkyl), cyano, halogen, hydroxy and (halo)$_{1-3}$(C$_{1-8}$) alkyl;

R$_5$ is selected from the group consisting of hydrogen and C$_{1-8}$ alkyl (optionally substituted on a terminal carbon atom with a substituent selected from the group consisting of amino (substituted with two substituents independently selected from the group consisting of hydrogen and C$_{1-4}$ alkyl), (halo)$_{1-3}$ and hydroxy) and aryl (optionally substituted with one to four substituents independently selected from the group consisting of C$_{1-8}$ alkyl and halogen); and, R$_6$ is selected from the group consisting of C$_{1-8}$ alkyl, aryl (C$_{1-8}$)alkyl, C$_{1-8}$ alkoxy, aryl(C$_{1-8}$)alkoxy, C$_{2-8}$ alkenyl, C$_{2-8}$ alkenyloxy, aryl(C$_{2-8}$)alkenyl, aryl(C$_{2-8}$)alkenyloxy, aryl, aryloxy and hydroxy.

Embodiments of the present invention include a process for making a benzolactone of Formula (C) comprising a) reacting an anhydride of Formula (F):

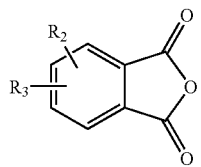

Formula (F)

with a compound of Formula (G):

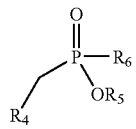

Formula (G)

under suitable conditions in the presence of an alkali metal (M) to provide a compound of Formula (H):

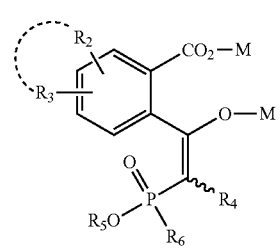

Formula (H)

b) and, reacting the compound of Formula (H) under conditions suitable to form the benzolactone of Formula (C):

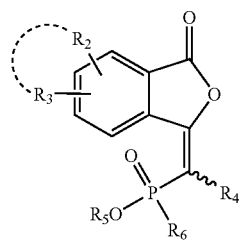

Formula (C)

wherein

R$_2$ and R$_3$ are attached to a benzene ring and independently selected from the group consisting of ca). hydrogen;

cb). C$_{1-4}$ alkyl optionally substituted on a terminal carbon atom with a substituent selected from the group consisting of amino (substituted with two substituents independently selected from the group consisting of hydrogen and C$_{1-4}$ alkyl), (halo)$_{1-3}$ and hydroxy;

cc). C$_{1-4}$ alkoxy optionally substituted on a terminal carbon atom with a substituent selected from the group consisting of (halo)$_{1-3}$ and hydroxy;

cd). C$_{2-4}$ alkenyl;

ce). amino substituted with two substituents independently selected from the group consisting of hydrogen and C$_{1-4}$ alkyl;

cf). halogen; and, cg). hydroxy;

optionally, R$_2$ and R$_3$ together form at least one ring fused to the benzene ring; thereby providing a multiple ring system; wherein the multiple ring system is selected from the group consisting of C$_9$-C$_{14}$ benzo fused cycloalkyl, C$_9$-C$_{14}$ benzo fused cycloalkenyl, C$_9$-C$_{14}$ benzo fused aryl, benzo fused heterocyclyl and benzo fused heteroaryl; and, wherein the multiple ring system can optionally be substituted with one to four substituents independently selected from the group consisting of da). C$_{1-4}$ alkyl optionally substituted on a terminal carbon atom with a substituent selected from the group consisting of amino (substituted with two substituents independently selected from the group consisting of hydrogen and C$_{1-4}$ alkyl), (halo)$_{1-3}$ and hydroxy;

db). C$_{1-4}$ alkoxy optionally substituted on a terminal carbon atom with a substituent selected from the group consisting of (halo)$_{1-3}$ and hydroxy;

dc). amino substituted with two substituents independently selected from the group consisting of hydrogen and C$_{1-4}$ alkyl;

dd). halogen;
de). hydroxy; and,
df. nitro;

$R_4$ is selected from the group consisting of $C_{1-4}$ alkyl (optionally substituted on a terminal carbon atom with a substituent selected from the group consisting of aryl and heteroaryl), aryl and heteroaryl; wherein aryl and heteroaryl and the aryl and heteroaryl portions of the substituted alkyl are optionally substituted with one to four substituents independently selected from the group consisting of $C_{1-4}$ alkyl, amino (substituted with two substituents independently selected from the group consisting of hydrogen and $C_{1-4}$ alkyl), cyano, halogen, hydroxy and $(halo)_{1-3}(C_{1-8})$ alkyl;

$R_5$ is selected from the group consisting of hydrogen and $C_{1-8}$ alkyl (optionally substituted on a terminal carbon atom with a substituent selected from the group consisting of amino (substituted with two substituents independently selected from the group consisting of hydrogen and $C_{1-4}$ alkyl), $(halo)_{1-3}$ and hydroxy) and aryl (optionally substituted with one to four substituents independently selected from the group consisting of $C_{1-8}$ alkyl and halogen); and $R_6$ is selected from the group consisting of $C_{1-8}$ alkyl, aryl $(C_{1-8})$alkyl, $C_{1-8}$ alkoxy, aryl$(C_{1-8})$alkoxy, $C_{2-8}$ alkenyl, $C_{2-8}$ alkenyloxy, aryl$(C_{2-8})$alkenyl, aryl$(C_{2-8})$alkenyloxy, aryl, aryloxy and hydroxy.

Embodiments of the present invention include compounds of Formula (II):

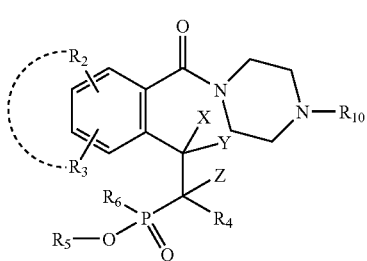

Formula (II)

wherein
$R_{10}$ is selected from the group consisting of:
a). sulfonyl substituted with a substituent selected from the group consisting of $C_{1-8}$ alkyl, aryl, aryl$(C_{1-8})$alkyl, aryl$(C_{2-8})$alkenyl, cycloalkyl, cycloalkenyl, heterocycyl, heteroaryl, heteroaryl$(C_{1-8})$alkyl and heteroaryl$(C_{2-8})$alkenyl;
b). carbonyl substituted with a substituent selected from the group consisting of $C_{1-8}$ alkyl, aryl, aryl$(C_{1-8})$alkyl, aryl$(C_{2-8})$alkenyl, cycloalkyl, cycloalkenyl, heterocycyl heteroaryl, heteroaryl$(C_{1-8})$alkyl, heteroaryl$(C_{2-8})$alkenyl, $-OR_{11}$, and amino (with two substituents independently selected from the group consisting of hydrogen, $C_{1-8}$ alkyl, aryl, aryl$C_{1-8}$ alkyl, arylcarbonyl, aryl$C_{1-8}$ alkyl carbonyl and heteroaryl $C_{1-8}$ alkyl);
c). $C_{1-8}$ alkyl optionally substituted on a terminal carbon atom with a substituent selected from the group consisting of aryl, cycloalkyl, cycloalkenyl, heterocycl, heteroaryl, $(halo)_{1-3}$, hydroxy, $-C(O)R_{12}$ and amino (with two substituents independently selected from the group consisting of hydrogen, $C_{1-8}$ alkyl, aryl$C_{1-8}$ alkyl, arylcarbonyl, aryl$C_{1-8}$ alkyl carbonyl and heteroaryl $C_{1-8}$ alkyl);
d). aryl;
e). heteroaryl;
f). cycloalkyl
g). cycloalkenyl; and,
h). heterocyclyl
wherein the heterocycyl, cycloalkyl, cycloalkenyl portion of a)., b)., and c)., the cylcoalkyl f)., cylcoalkenyl g)., and heterocyclyl h). are optionally substituted with one to two substituents independently selected from the group consisting of:
ea). oxo
eb). carbonyl substituted with a substituent selected from the group consisting of $C_{1-8}$ alkyl, aryl, aryl$(C_{1-8})$alkyl, aryl$(C_{2-8})$alkenyl, cycloalkyl, cycloalkenyl, heterocycl heteroaryl, heteroaryl$(C_{1-8})$alkyl, heteroaryl$(C_{2-8})$alkenyl and amino (with two substituents independently selected from the group consisting of hydrogen, $C_{1-8}$ alkyl, aryl$C_{1-8}$ alkyl, arylcarbonyl, aryl$C_{1-8}$ alkyl carbonyl and heteroaryl $C_{1-8}$ alkyl);
ec). $C_{1-8}$ alkyl optionally substituted with a substituent selected from the group consisting of amino (with two substituents independently selected from the group consisting of hydrogen, $C_{1-8}$ alkyl, aryl$C_{1-8}$ alkyl, arylcarbonyl, aryl$C_{1-8}$ alkyl carbonyl and heteroaryl $C_{1-8}$ alkyl), aryl, cycloalkyl, cycloalkenyl, heterocycl, heteroaryl, $(halo)_{1-3}$, and hydroxy;
ed). aryl; and
ef. $(halo)_{1-3}$
wherein the aryl portion of the a)., b)., c)., ec). and ed). substituents, the heteroaryl portion of the a)., b)., c). and ec). substituents and the d). aryl and e). heteroaryl substituents are optionally substituted with one to four substituents independently selected from the group consisting of
fa). $C_{1-4}$ alkyl optionally substituted on a terminal carbon atom with a substituent selected from the group consisting of aryl, cycloalkyl, cycloalkenyl, heterocycl, heteroaryl, $(halo)_{1-3}$, hydroxy, $-C(O)R_{12}$ and amino (with two substituents independently selected from the group consisting of hydrogen, $C_{1-8}$ alkyl, aryl$C_{1-8}$ alkyl, arylcarbonyl, aryl$C_{1-8}$ alkyl carbonyl and heteroaryl $C_{1-8}$ alkyl);
fb). $C_{2-4}$ alkenyl optionally substituted on a terminal carbon atom with a substituent selected from the group consisting of amino (with two substituents independently selected from the group consisting of hydrogen and $C_{1-8}$ alkyl), $(halo)_{1-3}$ and hydroxy;
fc). $C_{1-4}$ alkoxy optionally substituted on a terminal carbon atom with a substituent selected from the group consisting of $(halo)_{1-3}$ and hydroxy;
fd). cycloalkyl,
fe). heterocyclyl,
ff). aryl optionally substituted with one to four substituents independently selected from the group consisting of $C_{1-8}$ alkyl and halogen;
fg). heteroaryl,
fh). hydroxy;
fi). hydroxy;
fj). nitro; and
fk). $(halo)_{1-3}$;
wherein the aryl portion of the aryl$C_{1-8}$ alkyl, arylcarbonyl, aryl$C_{1-8}$ alkyl carbonyl of fa). are optionally substituted with one to four substituents independently selected from the group consisting of $C_{1-4}$ alkyl (optionally substituted on a terminal carbon atom with a substituent selected from the group consisting of amino (substituted with two substituents independently selected from the group consisting of hydrogen and $C_{1-8}$ alkyl), $(halo)_{1-3}$ and hydroxy), $C_{1-4}$ alkoxy (optionally substituted on a terminal carbon atom with a substituent selected from the group consisting of $(halo)_{1-3}$), amino (substituted with two substituents independently selected from the group consisting of hydrogen and $C_{1-4}$ alkyl), halogen, hydroxy and nitro.

DETAILED DESCRIPTION OF THE INVENTION

Figure 1:
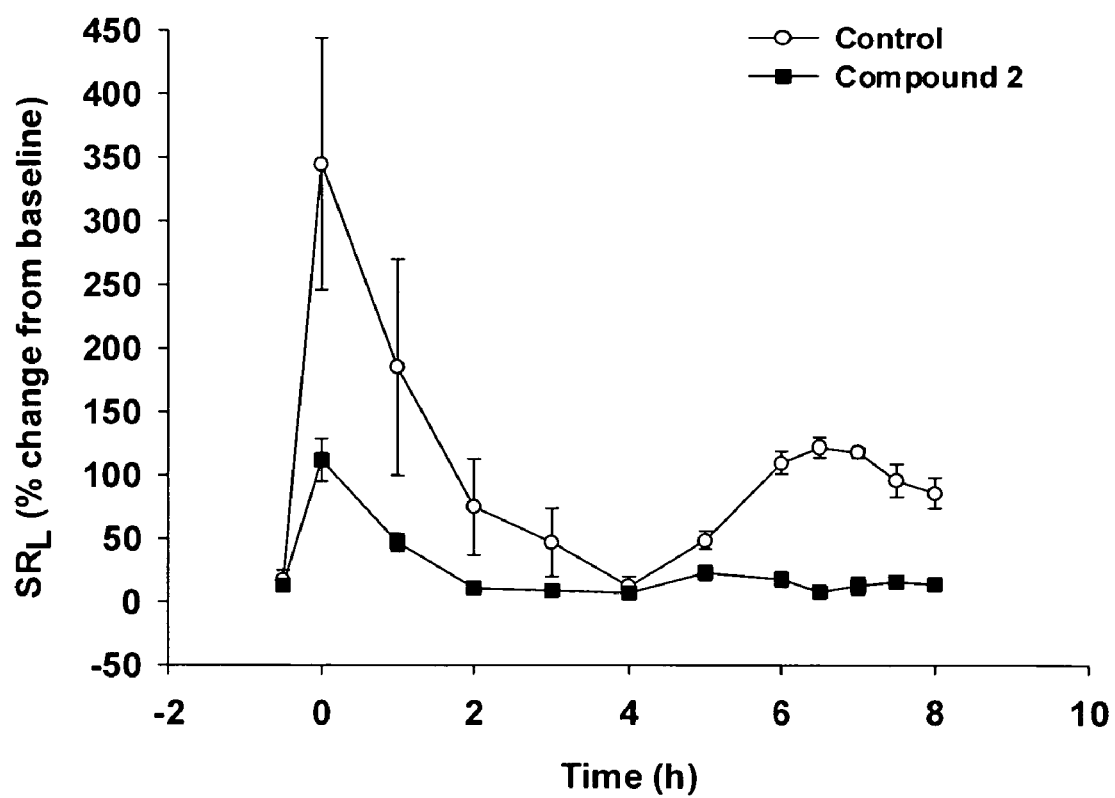
FIG. 1 shows the percent change in specific lung resistance ($SR_L$) from baseline for Compound 2 compared to control in a spontaneous *ascaris suum* antigen-induced model of asthma in sheep over an 8 hour period.

Embodiments of the present invention include those compounds wherein $R_1$ is selected from the group consisting of a heterocyclyl ring (wherein the point of attachment for the heterocyclyl ring at $R_1$ is a nitrogen ring atom) and —N($R_7R_8$); wherein the heterocyclyl ring is optionally substituted with a substituent selected from the group consisting of a). aryl($C_{1-4}$)alkyl, c). aryl, d). heteroaryl and i). heterocyclyl (optionally substituted with one to two substituents independently selected from the group consisting of oxo and aryl; and, optionally fused with the carbon of attachment to form a spiro heterocyclyl moiety); and, wherein the aryl portion of the a). and i). substituent and the c). aryl substituent are optionally substituted with one to two substituents independently selected from the group consisting of $C_{1-4}$ alkyl, $C_{1-4}$ alkoxy, aryl, heteroaryl, halogen, hydroxy, (halo)$_{1-3}$($C_{1-4}$)alkyl and (halo)$_{1-3}$($C_{1-4}$)alkoxy; and, all other variables are as previously defined.

Preferably, $R_1$ is selected from the group consisting of a heterocyclyl ring (wherein the point of attachment for the heterocyclyl ring at $R_1$ is a nitrogen ring atom) and —N($R_7R_8$); wherein the heterocyclyl ring is optionally substituted with a substituent selected from the group consisting of a). aryl($C_{1-4}$)alkyl, c). aryl, d). heteroaryl and i). heterocyclyl (optionally substituted with two substituents independently selected from the group consisting of oxo and aryl; and, optionally fused with the carbon of attachment to form a spiro heterocyclyl moiety); and, wherein the aryl portion of the a). and i). substituent and the c). aryl substituent are optionally substituted with one to two substituents independently selected from the group consisting of $C_{1-4}$ alkoxy and aryl; and, all other variables are as previously defined.

More preferably, $R_1$ is selected from the group consisting of pyrrolidinyl, piperidinyl and —N($R_7R_8$); wherein the point of attachment for pyrrolidinyl and piperidinyl is a nitrogen ring atom; and, wherein pyrrolidinyl and piperidinyl are optionally substituted with a substituent selected from the group consisting of a). phenylethyl, c). phenyl (optionally substituted with methoxy), d). benzothiazolyl and i). imidazolidinyl (optionally substituted with two substituents independently selected from the group consisting of oxo and phenyl; and, optionally fused with the carbon of attachment to form a spiro moiety); and, all other variables are as previously defined.

Most preferably, $R_1$ is selected from the group consisting of pyrrolidinyl, piperidinyl and —N($R_7R_8$); wherein the point of attachment for pyrrolidinyl and piperidinyl is a nitrogen ring atom in the one position; and, wherein pyrrolidinyl and piperidinyl are optionally substituted with a substituent selected from the group consisting of a). phenylethyl, c). phenyl (optionally substituted with methoxy), d). benzothiazolyl and i). imidazolidinyl (optionally substituted with two substituents independently selected from the group consisting of oxo and phenyl; and, optionally fused with the carbon of attachment to form a spiro moiety); and, all other variables are as previously defined.

Preferred embodiments of the present invention include those compounds wherein $R_7$ is selected from the group consisting of hydrogen, $C_{1-4}$ alkyl and $C_{2-4}$ alkenyl.

More preferably, $R_7$ is selected from the group consisting of hydrogen and $C_{1-4}$ alkyl.

Most preferably, $R_7$ is selected from the group consisting of hydrogen and methyl.

Embodiments of the present invention include those compounds wherein $R_8$ is selected from the group consisting of:

aa). $C_{1-8}$ alkyl optionally substituted on a terminal carbon atom with a substituent selected from the group consisting of cycloalkyl, heterocyclyl, (halo)$_{1-3}$ and hydroxy;

ab). cycloalkyl;

ac). cycloalkenyl; and, ad). heterocyclyl (wherein the point of attachment at $R_8$ is a carbon ring atom); wherein the ab). cycloalkyl, ac). cycloalkenyl and ad). heterocyclyl substituents (wherein the ad). heterocyclyl contains at least one nitrogen ring atom) and the cycloalkyl portion of the aa). substituent are optionally substituted with one to four substituents independently selected from the group consisting of:

ba). $C_{1-8}$ alkyl optionally substituted on a terminal carbon atom with a substituent selected from the group consisting of amino (with two substituents independently selected from the group consisting of hydrogen and $C_{1-8}$ alkyl), (halo)$_{1-3}$ and hydroxy;

bb). $C_{1-8}$ alkoxy;

bc). carbonyl substituted with a substituent selected from the group consisting of $C_{1-8}$ alkyl, aryl, aryl($C_{1-8}$)alkyl, aryl($C_{2-8}$)alkenyl, heteroaryl, heteroaryl($C_{1-8}$)alkyl and heteroaryl($C_{2-8}$)alkenyl;

bd). aryl;

be). heteroaryl;

bf). amino substituted with two substituents independently selected from the group consisting of hydrogen and $C_{1-8}$ alkyl;

bh). halogen;

bi). hydroxy;

bk). heterocyclyl; and, bl). sulfonyl substituted with a substituent selected from the group consisting of $C_{1-8}$ alkyl, aryl, aryl($C_{1-8}$)alkyl, aryl($C_{2-8}$)alkenyl, heteroaryl, heteroaryl($C_{1-8}$)alkyl and heteroaryl($C_{2-8}$)alkenyl;

wherein the bd). aryl, be). heteroaryl and bk). heterocyclyl substituents and the aryl and heteroaryl portions of the bc). substituent are optionally substituted with one to four substituents independently selected from the group consisting of $C_{1-4}$ alkyl (optionally substituted on a terminal carbon atom with a substituent selected from the group consisting of (halo)$_{1-3}$), $C_{1-4}$ alkoxy, amino (substituted with two substituents independently selected from the group consisting of hydrogen and $C_{1-4}$ alkyl), halogen and hydroxy;

and, provided that the optional substituent attached to the ad). heterocyclyl nitrogen ring atom is not selected from the group consisting of bf). amino (substituted with two substituents independently selected from the group consisting of hydrogen and $C_{1-8}$ alkyl), bh). halogen, bi). hydroxy and bj). nitro.

Preferably, $R_8$ is selected from the group consisting of aa). cycloalkyl($C_{1-4}$)alkyl, ab). cycloalkyl, ac). cycloalkenyl and ad). heterocyclyl (wherein the point of attachment for the ad). heterocyclyl at $R_8$ is a carbon ring atom; and, the ad). heterocyclyl contains a single nitrogen ring atom); wherein the ab). cycloalkyl, ac). cycloalkenyl and ad). heterocyclyl substituents and the cycloalkyl portion of the aa). substituent are optionally substituted with one to two substituents independently selected from the group consisting of ba). $C_{1-4}$ alkyl, bc). carbonyl (substituted with a substituent selected from the group consisting of $C_{1-4}$ alkyl, aryl, aryl($C_{1-4}$)alkyl and aryl ($C_{2-4}$)alkenyl) and bd). aryl; wherein the bd). aryl substituent and the aryl portions of the bc). substituent are optionally substituted with one to two substituents independently selected from the group consisting of $C_{1-4}$ alkyl, $C_{1-4}$ alkoxy, di($C_{1-4}$ alkyl)amino, halogen, hydroxy and (halo)$_{1-3}$($C_{1-4}$) alkyl.

More preferably, $R_8$ is selected from the group consisting of aa). adamant-1-ylmethyl, ab). cyclopentyl, ab). cyclohexyl, ac). cyclohexenyl, ad). pyrrolidinyl and ad). piperidinyl (wherein the point of attachment for pyrrolidinyl and piperidinyl at $R_8$ is a carbon ring atom); wherein ab). cyclohexyl, ac). cyclohexenyl, ad). pyrrolidinyl and ad). piperidinyl are optionally substituted with one to two substituents independently selected from the group consisting of ba). $C_{1-4}$ alkyl, bc). carbonyl (substituted with a substituent selected from the group consisting of $C_{1-4}$ alkyl, aryl, aryl($C_{1-4}$)alkyl and aryl($C_{2-4}$)alkenyl) and bd). aryl; wherein the bd). aryl substituent and the aryl portions of the bc). substituent are optionally substituted with one to two substituents independently selected from the group consisting of $C_{1-4}$ alkyl, $C_{1-4}$ alkoxy, di($C_{1-4}$ alkyl)amino, halogen, hydroxy and (halo)$_{1-3}$($C_{1-4}$)alkyl.

Most preferably, $R_8$ is selected from the group consisting of aa). adamant-1-ylmethyl, ab). cyclopentyl, ab). cyclohexyl, ac). cyclohexenyl, ad). pyrrolidinyl and ad). piperidinyl (wherein the point of attachment for pyrrolidinyl and piperidinyl at $R_8$ is a carbon ring atom); wherein ab). cyclohexyl, ac). cyclohexenyl, ad). pyrrolidinyl and ad). piperidinyl are optionally substituted with one to two substituents independently selected from the group consisting of ba). methyl, ba). t-butyl, bc). methylcarbonyl, bc). i-propylcarbonyl, bc). phenylcarbonyl, bc). naphthalenylcarbonyl, bc). phenethylcarbonyl, bc). phenethenylcarbonyl and bd). phenyl; and, wherein the bd). phenyl substituent and the phenyl and naphthalenyl portions of the bc). substituent are optionally substituted with one to two substituents independently selected from the group consisting of methyl, methoxy, N,N-dimethylamino, fluorine, bromine, hydroxy and trifluoromethyl.

Embodiments of the present invention include those compounds wherein $R_2$ and $R_3$ are attached to the benzene ring (shown in Formula I) on adjacent carbon atoms. Preferred embodiments of the present invention include those compounds wherein $R_2$ and $R_3$ are independently selected from the group consisting of ca). hydrogen, cb). $C_{1-4}$ alkyl, cc). $C_{1-4}$ alkoxy, cd). $C_{2-4}$ alkenyl, ce). amino (substituted with two substituents independently selected from the group consisting of hydrogen and $C_{1-4}$ alkyl), cf. halogen and cg). hydroxy; optionally $R_2$ and $R_3$ together form at least one ring fused to the benzene ring; thereby providing a multiple ring system; wherein the multiple ring system is selected from the group consisting of naphthalene and anthracene; and, wherein the multiple ring system can optionally be substituted with one to four substituents independently selected from the group consisting of da). $C_{1-4}$ alkyl, db). $C_{1-4}$ alkoxy, dc). amino (substituted with two substituents independently selected from the group consisting of hydrogen and $C_{1-4}$ alkyl), dd). halogen and de). hydroxy.

More preferably, $R_2$ and $R_3$ are attached to the benzene ring on adjacent carbon atoms and independently selected from the group consisting of ca). hydrogen, cb). $C_{1-4}$ alkyl, cd). $C_{2-4}$ alkenyl, cf). halogen and cg). hydroxy; optionally, $R_2$ and $R_3$ together form at least one ring fused to the benzene ring; thereby providing a multiple ring system; wherein the multiple ring system is naphthalene; and, wherein the multiple ring system can optionally be substituted with one to four substituents independently selected from the group consisting of da). $C_{1-4}$ alkyl, db). $C_{1-4}$ alkoxy, dc). amino (substituted with two substituents independently selected from the group consisting of hydrogen and $C_{1-4}$ alkyl), dd). halogen and de). hydroxy.

Most preferably, the multiple ring system is a non-substituted naphthalene.

Embodiments of the present invention include those compounds wherein $R_4$ is selected from the group consisting of aryl and heteroaryl optionally substituted with one to two substituents independently selected from the group consisting of $C_{1-4}$ alkyl, amino (substituted with two substituents independently selected from the group consisting of hydrogen and $C_{1-4}$ alkyl), cyano, halogen, hydroxy and (halo)$_{1-3}$($C_{1-8}$)alkyl.

Preferably, $R_4$ is selected from the group consisting of aryl and heteroaryl (wherein heteroaryl is optionally substituted with one to two substituents independently selected from the group consisting of $C_{1-4}$ alkyl, amino (substituted with two substituents independently selected from the group consisting of hydrogen and $C_{1-4}$ alkyl), cyano, halogen, hydroxy and (halo)$_{1-3}$($C_{1-8}$)alkyl).

More preferably, $R_4$ is selected from the group consisting of phenyl, naphthalenyl and benzothienyl (wherein benzothienyl is optionally substituted with one to two halogen substituents).

Most preferably, $R_4$ is selected from the group consisting of phenyl, naphthalenyl and benzothienyl (wherein benzothienyl is optionally substituted with a chloro substituent).

Embodiments of the present invention include those compounds wherein $R_5$ is selected from the group consisting of hydrogen and $C_{1-4}$ alkyl (optionally substituted on a terminal carbon atom with a substituent selected from the group consisting of amino (substituted with two substituents independently selected from the group consisting of hydrogen and $C_{1-4}$ alkyl), (halo)$_{1-3}$ and hydroxy).

Preferably, $R_5$ is selected from the group consisting of hydrogen and $C_{1-4}$ alkyl.

More preferably, $R_5$ is selected from the group consisting of hydrogen and methyl.

Most preferably, $R_5$ is hydrogen.

Preferred embodiments of the present invention include those compounds wherein $R_6$ is selected from the group consisting of $C_{1-4}$ alkyl, aryl($C_{1-4}$)alkyl, $C_{1-4}$ alkoxy, aryl($C_{1-4}$) alkoxy, $C_{2-4}$ alkenyl, $C_{2-4}$ alkenyloxy, aryl($C_{2-4}$)alkenyl, aryl ($C_{2-4}$)alkenyloxy, aryl, aryloxy and hydroxy.

More preferably, $R_6$ is selected from the group consisting of methyl, methoxy, phenyloxy and hydroxy.

Most preferably, $R_6$ is selected from the group consisting of methyl and hydroxy.

Preferred embodiments of the present invention include those compounds wherein Y is not present and X is one substituent attached by a double-bond selected from the group consisting of O, S, imino, ($C_{1-4}$)alkylimino and hydroxyimino.

More preferably, Y is not present and X is one substituent attached by a double-bond selected from the group consisting of O, imino and hydroxyimino.

Most preferably, Y is not present and X is O attached by a double-bond.

Preferred embodiments of the present invention include those compounds wherein Z is selected from the group consisting of hydrogen and $C_{1-4}$ alkyl.

More preferably, Z is hydrogen.

Embodiments of the present invention include those compounds of Formula (Ia) shown in Table 1.

TABLE 1

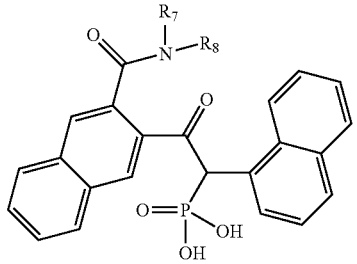

Formula (Ia)

wherein
$R_5$, $R_7$ and $R_8$ are dependently selected from the group consisting of:

| Cpd | $R_7$ | $R_8$ |
|---|---|---|
| 1 | CH$_3$ | 4-phenylcyclohexyl |
| 2 | CH$_3$ | 1-(2-naphthalenylcarbonyl)-4-piperidinyl |
| 3 | CH$_3$ | 1-[(6-methoxy-2-naphthalenyl)carbonyl]-3-pyrrolidinyl |
| 4 | CH$_3$ | 1-[(6-bromo-2-naphthalenyl)carbonyl]-4-piperidinyl |
| 5 | CH$_3$ | 1-[3-(4-fluorophenyl)-1-oxo-2-propenyl]-3-pyrrolidinyl |
| 6 | CH$_3$ | 1-[1-oxo-3-phenyl-2-propenyl]-4-piperidinyl |
| 9 | CH$_3$ | 1-[3-(4-methylphenyl)-1-oxo-2-propenyl]-4-piperidinyl |
| 10 | CH$_3$ | 1-[1-oxo-3-[4-(trifluoromethyl)phenyl]-2-propenyl]-4-piperidinyl |
| 13 | CH$_3$ | 1-[3-[4-(dimethylamino)phenyl]-1-oxo-2-propenyl]-4-piperidinyl |
| 15 | CH$_3$ | 1-benzoyl-4-piperidinyl |
| 17 | CH$_3$ | Cyclohexyl |
| 18 | CH$_3$ | 1-[1-oxo-3-[4-(trifluoromethyl)phenyl]propyl]-4-piperidinyl |
| 20 | CH$_3$ | 1-(2-methyl-1-oxopropyl)-4-piperidinyl |
| 21 | CH$_3$ | Cyclopentyl |
| 22 | CH$_3$ | 4-(1,1-dimethylethyl)cyclohexyl |
| 24 | CH$_3$ | 1-[(6-hydroxy-2-naphthalenyl)carbonyl]-4-piperidinyl |
| 26 | CH$_3$ | 1-acetyl-4-piperidinyl |
| 27 | CH$_3$ | 4-methylcyclohexyl |
| 28 | CH$_3$ | adamant-1-ylmethyl |
| 29 | CH$_3$ | 4-phenyl-3-cyclohexen-1-yl |
| And, | | |
| 30 | H | 1-(2-naphthalenylcarbonyl)-4-piperidinyl | and racemates, enantiomers, diastereomers and salts thereof.

Embodiments of the present invention include those compounds of Formula (Ib) shown in Table 2.

TABLE 2

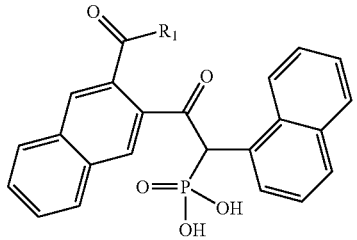

Formula (Ib)

wherein
$R_1$ is selected from the group consisting of:

| Cpd | $R_1$ |
|---|---|
| 7 | 4-phenyl-1-piperidinyl |
| 8 | 4-oxo-1-phenyl-1,3,8-triazaspiro[4.5]dec-8-yl |
| 12 | 4-(4-methoxyphenyl)-1-piperidinyl |
| 14 | 4-(3-methoxyphenyl)-1-piperidinyl |

TABLE 2-continued

| | |
|---|---|
| 16 | 4-(2-benzothiazolyl)-1-piperidinyl |
| 19 | 3-phenyl-1-pyrrolidinyl |
| and, | |
| 25 | 3-(2-phenylethyl)-1-pyrrolidinyl | and racemates, enantiomers, diastereomers and salts thereof.

Embodiments of the present invention include those compounds of Formula (Ic) shown in Table 3.

TABLE 3

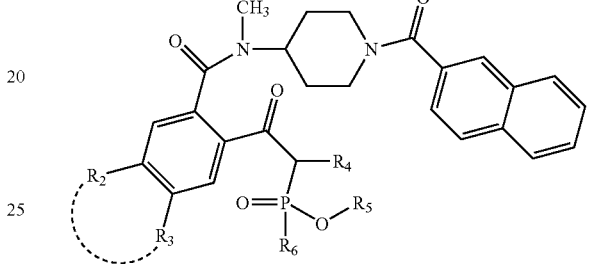

Formula (Ic)

wherein $R_2$, $R_3$, $R_4$, $R_5$ and $R_6$ are dependently selected from the group consisting of:

| Cpd | $R_2$ | $R_3$ | $R_4$ | $R_5$ | $R_6$ |
|---|---|---|---|---|---|
| 11 | taken together to form phenyl | | phenyl | H | OH |
| 23 | taken together to form phenyl | | 1-naphthalenyl | CH$_3$ | OH |
| 31 | H | H | 1-naphthalenyl | H | OH |
| 32 | taken together to form phenyl | | 1-naphthalenyl | H | CH$_3$ |
| And, | | | | | |
| 33 | taken together to form phenyl | | 5-chloro-benzo[b]thien-3-yl | H | OH | and racemates, enantiomers, diastereomers and salts thereof.

In embodiments for Formula (II) the preferred embodiments of $R_2$, $R_3$, $R_4$, $R_5$ and $R_6$ are as previously described.

Preferably, $R_{10}$ is selected from the group consisting of a). sulfonyl substituted with a substituent selected from the group consisting of $C_{1-8}$ alkyl, aryl, aryl($C_{1-8}$)alkyl, aryl ($C_{2-8}$)alkenyl, cycloalkyl, cycloalkenyl, heterocycl, heteroaryl, heteroaryl($C_{1-8}$)alkyl and heteroaryl($C_{2-8}$)alkenyl;

b). carbonyl substituted with a substituent selected from the group consisting of $C_{1-8}$ alkyl, aryl, aryl($C_{1-8}$)alkyl, aryl ($C_{2-8}$)alkenyl, cycloalkyl, cycloalkenyl, heterocycl heteroaryl, heteroaryl($C_{1-8}$)alkyl, heteroaryl($C_{2-8}$)alkenyl, —OR$_{11}$ and amino (with two substituents independently selected from the group consisting of hydrogen, $C_{1-8}$ alkyl, aryl, arylC$_{1-8}$ alkyl, arylcarbonyl, arylC$_{1-8}$ alkyl carbonyl and heteroaryl $C_{1-8}$ alkyl);

c). $C_{1-8}$ alkyl optionally substituted on a terminal carbon atom with a substituent selected from the group consisting of aryl, cycloalkyl, cycloalkenyl, heterocycl, heteroaryl, (halo)$_{1-3}$, hydroxy, —C(O)R$_{12}$ and amino (with two substituents independently selected from the group consisting of hydrogen, $C_{1-8}$ alkyl, arylC$_{1-8}$ alkyl, arylcarbonyl, arylC$_{1-8}$ alkyl carbonyl and heteroaryl $C_{1-8}$ alkyl);

d). aryl; and
e). heteroaryl;
wherein the heterocycl, cycloalkyl, cycloalkenyl portion of a)., b)., and c). are optionally substituted with one to two substituents independently selected from the group consisting of:
  ea). oxo
  eb). carbonyl substituted with a substituent selected from the group consisting of $C_{1-8}$ alkyl, aryl, aryl($C_{1-8}$)alkyl, aryl($C_{2-8}$)alkenyl, cycloalkyl, cycloalkenyl, heterocycl heteroaryl, heteroaryl($C_{1-8}$)alkyl, heteroaryl($C_{2-8}$)alkenyl and amino (with two substituents independently selected from the group consisting of hydrogen, $C_{1-8}$ alkyl, aryl$C_{1-8}$ alkyl, arylcarbonyl, aryl$C_{1-8}$ alkyl carbonyl and heteroaryl $C_{1-8}$ alkyl);
  ec). $C_{1-8}$ alkyl optionally substituted with a substituent selected from the group consisting of amino (with two substituents independently selected from the group consisting of hydrogen, $C_{1-8}$ alkyl, aryl$C_{1-8}$ alkyl, arylcarbonyl, aryl$C_{1-18}$ alkyl carbonyl and heteroaryl $C_{1-8}$ alkyl), aryl, cycloalkyl, cycloalkenyl, heterocycl, heteroaryl, (halo)$_{1-3}$, and hydroxy;
  ed). aryl; and
  ef). (halo)$_{1-3}$
wherein the aryl portion of the a)., b)., c)., ec). and ed). substituents, the heteroaryl portion of the a)., b)., c). and ec). substituents and the d). aryl and e). heteroaryl substituents are optionally substituted with one to four substituents independently selected from the group consisting of
  fa). $C_{1-4}$ alkyl optionally substituted on a terminal carbon atom with a substituent selected from the group consisting of aryl, cycloalkyl, cycloalkenyl, heterocycl, heteroaryl, (halo)$_{1-3}$, hydroxy, —C(O)R$_{12}$ and amino (with two substituents independently selected from the group consisting of hydrogen, $C_{1-8}$ alkyl, aryl$C_{1-8}$ alkyl, arylcarbonyl, aryl$C_{1-8}$ alkyl carbonyl and heteroaryl $C_{1-8}$ alkyl);
  fb). $C_{2-4}$ alkenyl optionally substituted on a terminal carbon atom with a substituent selected from the group consisting of amino (with two substituents independently selected from the group consisting of hydrogen and $C_{1-8}$ alkyl), (halo)$_{1-3}$ and hydroxy;
  fc). $C_{1-4}$ alkoxy optionally substituted on a terminal carbon atom with a substituent selected from the group consisting of (halo)$_{1-3}$ and hydroxy;
  fd). cycloalkyl,
  fe). heterocyclyl,
  ff). aryl optionally substituted with one to four substituents independently selected from the group consisting of $C_{1-8}$ alkyl and halogen;
  fg). heteroaryl,
  fh). hydroxy;
  fi). hydroxy;
  fj). nitro; and
  fk). (halo)$_{1-3}$;
wherein the aryl portion of the aryl$C_{1-8}$ alkyl, arylcarbonyl, aryl$C_{1-8}$ alkyl carbonyl of fa). are optionally substituted with one to four substituents independently selected from the group consisting of $C_{1-4}$ alkyl (optionally substituted on a terminal carbon atom with a substituent selected from the group consisting of amino (substituted with two substituents independently selected from the group consisting of hydrogen and $C_{1-8}$ alkyl), (halo)$_{1-3}$ and hydroxy), $C_{1-4}$ alkoxy (optionally substituted on a terminal carbon atom with a substituent selected from the group consisting of (halo)$_{1-3}$), amino (substituted with two substituents independently selected from the group consisting of hydrogen and $C_{1-4}$ alkyl), halogen, hydroxy and nitro.

Preferably, R$_{11}$ is selected from the group consisting of:
  aa). $C_{1-4}$ alkyl optionally substituted on a terminal carbon atom with a substituent selected from the group consisting of cycloalkyl, heterocyclyl, aryl, heteroaryl, amino (with two substituents independently selected from the group consisting of hydrogen and $C_{1-4}$ alkyl), (halo)$_{1-3}$ and hydroxy;
wherein the cycloalkyl, heterocyclyl, aryl and heteroaryl portions of the aa). substituent are optionally substituted with one to four substituents independently selected from the group consisting of:
  ba). $C_{1-4}$ alkyl optionally substituted on a terminal carbon atom with a substituent selected from the group consisting of amino (with two substituents independently selected from the group consisting of hydrogen and $C_{1-4}$ alkyl), (halo)$_{1-3}$ and hydroxy;
  bb). $C_{1-4}$ alkoxy optionally substituted on a terminal carbon atom with a substituent selected from the group consisting of carboxyl, (halo)$_{1-3}$ and hydroxy;
  bc). carbonyl substituted with a substituent selected from the group consisting of $C_{1-4}$ alkyl, aryl, aryl($C_{1-4}$)alkyl, aryl($C_{2-4}$)alkenyl, heteroaryl, heteroaryl($C_{1-4}$)alkyl and heteroaryl($C_{2-4}$)alkenyl;
  bd). aryl;
  be). heteroaryl;
  bf). amino substituted with two substituents independently selected from the group consisting of hydrogen and $C_{1-4}$ alkyl;
  bh). (halo)$_{1-3}$;
  bi). hydroxy; and
  bk). heterocyclyl optionally substituted with one to two oxo substituents; and,
wherein the bd). aryl, be). heteroaryl and bk). heterocyclyl substituents and the aryl and heteroaryl portions of the bc). substituent are optionally substituted with one to four substituents independently selected from the group consisting of $C_{1-4}$ alkyl (optionally substituted on a terminal carbon atom with a substituent selected from the group consisting of amino (substituted with two substituents independently selected from the group consisting of hydrogen and $C_{1-4}$ alkyl), (halo)$_{1-3}$ and hydroxy), $C_{1-4}$ alkoxy (optionally substituted on a terminal carbon atom with a substituent selected from the group consisting of (halo)$_{1-3}$), amino (substituted with two substituents independently selected from the group consisting of hydrogen and $C_{1-4}$ alkyl), halogen, hydroxy and nitro;

Preferably, R$_{12}$ is selected from the group consisting of $C_{1-4}$ alkyl, aryl, aryl($C_{1-4}$)alkyl, aryl($C_{2-4}$)alkenyl, cycloalkyl, cycloalkenyl, heterocycl heteroaryl, heteroaryl($C_{1-4}$)alkyl, heteroaryl($C_{2-4}$)alkenyl, —OR$_{11}$ and amino (with two substituents independently selected from the group consisting of hydrogen, $C_{1-4}$ alkyl, aryl$C_{1-4}$ alkyl, arylcarbonyl, aryl$C_{1-4}$ alkyl carbonyl and heteroaryl $C_{1-4}$ alkyl); wherein the aryl, the heteroaryl portion of R$_{12}$ are optionally substituted with one to four substituents independently selected from the group consisting of:
  fa). $C_{1-4}$ alkyl optionally substituted on a terminal carbon atom with a substituent selected from the group consisting of aryl, cycloalkyl, cycloalkenyl, heterocycl, heteroaryl, (halo)$_{1-3}$, hydroxy, —C(O)R$_{11}$ and amino (with two substituents independently selected from the group consisting of hydrogen, $C_{1-8}$ alkyl, aryl$C_{1-4}$ alkyl, arylcarbonyl, aryl$C_{1-4}$ alkyl carbonyl and heteroaryl $C_{1-4}$ alkyl);
  fb). $C_{2-4}$ alkenyl optionally substituted on a terminal carbon atom with a substituent selected from the group consisting of amino (with two substituents independently selected from the group consisting of hydrogen and $C_{1-4}$ alkyl), $(halo)_{1-3}$ and hydroxy;

fc). $C_{1-4}$ alkoxy optionally substituted on a terminal carbon atom with a substituent selected from the group consisting of $(halo)_{1-3}$ and hydroxy;

fd). cycloalkyl, fe). heterocyclyl, ff). aryl optionally substituted with one to four substituents independently selected from the group consisting of $C_{1-4}$ alkyl and halogen;

fg). heteroaryl, fh). $(halo)_{1-3}$;

fi). hydroxy; and fj). nitro;

wherein the aryl portion of the aryl$C_{1-8}$ alkyl, arylcarbonyl, aryl$C_{1-8}$ alkyl carbonyl of fa). are optionally substituted with one to four substituents independently selected from the group consisting of $C_{1-4}$ alkyl (optionally substituted on a terminal carbon atom with a substituent selected from the group consisting of amino (substituted with two substituents independently selected from the group consisting of hydrogen and $C_{1-8}$ alkyl), $(halo)_{1-3}$ and hydroxy), $C_{1-4}$ alkoxy (optionally substituted on a terminal carbon atom with a substituent selected from the group consisting of $(halo)_{1-3}$), amino (substituted with two substituents independently selected from the group consisting of hydrogen and $C_{1-4}$ alkyl), halogen, hydroxy and nitro;

Embodiments of the present invention include those compounds of Formula (IIa) shown in Table 4.

TABLE 4

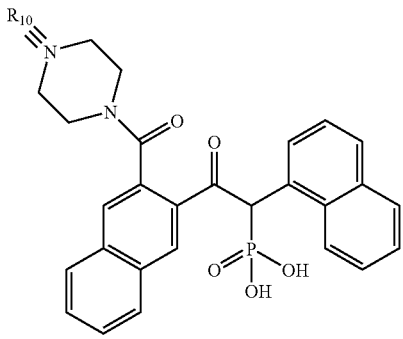

| Cpd | $R_{10}$ |
|---|---|
| 37 | naphthalene-2-yl-acetyl |
| 38 | 2-naphthoyl |
| 39 | 1-(4-hydroxyphenyl) |
| 40 | 1-(4-methoxyphenyl) |
| 41 | N-[5-(sulfonyl)-thiophene-2-ylmethyl]-benzamide |
| 42 | 6-chloro-5-sulfonyl-imidazo[2,1-b]thiazole |
| 43 | Naphthyl-2-aminocarbonyl |
| 44 | 1-(4-fluorophenyl) | and racemates, enantiomers, diastereomers and salts thereof.

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p 1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, SEH, sodium, sodium carbonate, sodium-2-ethylhexanoate, sodium hydroxide, triethanolamine (TEA) or zinc.

Compounds of the present invention may be contacted with a pharmaceutically acceptable cation selected from the group consisting of aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, SEH, sodium, sodium carbonate, sodium-2-ethylhexanoate, sodium hydroxide, triethanolamine (TEA) and zinc to form a salt.

Preferred cations for use with the instant compounds are selected from the group consisting of benzathine, t-butylamine, calcium gluconate, calcium hydroxide, choline bicarbonate, choline chloride, cyclohexylamine, diethanolamine, ethylenediamine, LiOMe, L-lysine, $NH_3$, $NH_4OH$, N-methyl-D-glucamine, piperidine, potassium-t-butoxide, potassium hydroxide (aqueous), procaine, quinine, sodium carbonate, sodium-2-ethylhexanoate, sodium hydroxide, triethanolamine and tromethane.

More preferably, cations for use with the instant compounds are selected from the group consisting of t-butylamine, $NH_4OH$ and tromethane.

Most preferably, the cation for use with the instant compounds is tromethane.

The present invention includes within its scope prodrugs of the compounds of this invention. In general, such prodrugs will be functional derivatives of the compounds, which are readily convertible in vivo into an active compound. Thus, in the methods of treatment of the present invention, the term "administering" shall encompass the treatment of the various disorders described with the compound specifically disclosed or a prodrug compound which would be obviously included within the scope of the invention although not specifically disclosed including, but not limited to diphenylphosphonate or diphenylphosphinate esters of certain of the instant compounds. Conventional procedures for the selection and preparation of suitable prodrug derivatives are described, for example, in "*Design of Prodrugs*", ed. H. Bundgaard, Elsevier, 1985. Phosphonic acid prodrugs (as described in De Lombaert S., et al, Non-Peptidic Inhibitors of Neutral Endopeptidase 24.11; Design and Pharmacology of Orally Active Phosphonate Prodrugs, *Bioorganic and Medicinal Chemistry Letters,* 1995, 5(2), 151-154; and, De Lombaert S., et al, N-Phosphonomethyl Dipeptides and Their Phosphonate Prodrugs, a New Generation Neutral Endopeptidase (NEP, EC 3.424.11) Inhibitors, *J. Med. Chem.,* 1994, 37, 498-511) and phosphinic acid prodrugs are intended to be included within the scope of the present invention.

The compounds according to this invention may have at least one chiral center and thus may exist as enantiomers. In addition, the compounds of the present invention may also possess two or more chiral centers and thus may also exist as diastereomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active base, followed by fractional crystallization and regeneration of the compounds of this invention. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

The compounds according to this invention wherein Z forms a double bond with the carbon of attachment for X, Y is not present and X is hydroxy may have at least one keto-enol tautomeric form and thus may exist in equilibrium as geometric isomers. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, "alkyl" whether used alone or as part of a substituent group refers to straight and branched carbon chains having 1 to 8 carbon atoms or any number within this range. The term "alkoxy" refers to an —O-alkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a terminal carbon atom or, when acting as a linking group, within the carbon chain.

The term "cycloalkyl" refers to saturated, monocyclic or polycyclic hydrocarbon rings of from 3 to 20 carbon atom members (preferably from 3 to 12 carbon atom members). Further, a cycloalkyl ring may optionally be fused to one or more cycloalkyl rings. Examples of such rings include, and are not limited to, cyclopropyl, cyclobutyl, cyclopentyl, cyclohexyl, cycloheptyl or adamantyl.

The term "cycloalkenyl" refers to partially unsaturated, nonaromatic monocyclic or polycyclic hydrocarbon rings of 3 to 20 carbon atom members (preferably from 3 to 12 carbon atom members). Typically, a 3 to 5 member ring contains one double bond and a 6 to 9 member ring contains multiple double bonds. Further, a cycloalkenyl ring may optionally be fused to one or more cycloalkyl rings or cycloalkenyl rings. Examples of such rings include, and are not limited to, cyclopropenyl, cyclobutenyl, cyclopentenyl, cyclohexenyl, or cycloheptenyl.

The term "heterocyclyl" refers to a nonaromatic cyclic ring of 5 to 8 members in which 1 to 4 members are nitrogen or a nonaromatic cyclic ring of 5 to 8 members in which zero, one or two members are nitrogen and one member is oxygen or sulfur; wherein, optionally, the ring contains zero, one or two unsaturated bonds. Alternatively, the heterocyclyl ring may be fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, the heterocyclyl can be bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl. In the present invention, when $R_1$ is selected from heterocyclyl, the term "heterocyclyl" refers to a nonaromatic cyclic ring of 5 to 8 members in which 1 to 4 members are nitrogen; wherein, the point of attachment for the heterocyclyl ring at $R_1$ is a nitrogen ring member; and, wherein optionally the ring contains zero, one (for 5 and 6 member rings) or two (for 6, 7 and 8 member rings) unsaturated bonds.

The term "aryl" refers to an unsaturated, aromatic monocyclic ring of 6 carbon members or to an unsaturated, aromatic polycyclic ring of from 10 to 20 carbon members. Further, an aryl ring may optionally be fused to one or more benzene rings (benzo fused aryl), cycloalkyl rings (e.g. benzo fused cycloalkyl) or cycloalkenyl rings (e.g. benzo fused cycloalkenyl) wherein, for the purpose of these definitions, the cycloalkyl rings and cycloalkenyl rings may be fused to an additional benzene ring (to provide fused multiple ring systems such as fluorene). Examples of such aryl rings include, and are not limited to, phenyl, naphthalenyl, fluorenyl, indenyl or anthracenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to two additional nitrogens. In the case of 6 membered rings, the heteroaryl ring may contain from one to three nitrogen atoms. For the case wherein the 6 member ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered alicyclic ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

As used herein, the term "carboxyl" refers to the linking group —C(O)O— or (when used accordingly) to the substituent —COOH; the term "imino" refers to the substituent HN=.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. However, for clarity in the terms "$C_9$-$C_{14}$ benzo fused cycloalkyl", "$C_9$-$C_{14}$ benzo fused cycloalkenyl", "$C_9$-$C_{14}$ benzo fused aryl"; $C_9$-$C_{14}$ refers to the number of carbon atoms both in the benzene ring (6) and the number of atoms in the ring fused to the benzene ring, but does not include carbon atoms that may be pendent from these multiple ring systems. The amount of substituents attached to a moiety "optionally substituted with one to five substituents" is limited to that amount of open valences on the moiety available for substitution.

In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$alkyl" substituent refers to a group of the formula:

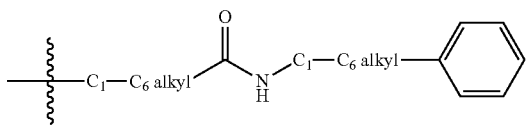

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Illustrative of the invention is a composition comprising a pharmaceutically acceptable carrier and any of the compounds described above. Also illustrative of the invention is a composition made by mixing any of the compounds described above and a pharmaceutically acceptable carrier. A further illustration of the invention is a process for making a composition comprising mixing any of the compounds described above and a pharmaceutically acceptable carrier. The present invention also provides compositions comprising one or more compounds of this invention in association with a pharmaceutically acceptable carrier.

The compounds of the present invention are useful serine protease inhibitors (in particular, inhibitors of cathepsin G and chymase) useful for treating inflammatory and serine protease mediated disorders. Some of these disorders include, inflammatory and serine protease mediated disorders include, and are not limited to, pulmonary inflammatory conditions, chronic obstructive pulmonary diseases, asthma, pulmonary emphysema, bronchitis, psoriasis, allergic rhinitis, viral rhinitis, ischemia, arthritis, glomerulonephritis, postoperative adhesion formation and reperfusion injury. These compounds would be useful in treating disease states caused by angiotensin II including but not limited to hypertension, hypercardia myocardial infarction, arteriosclerosis, diabetic and non-diabetic retinopathy, vascular restenosis and the like. Additionally, these compounds can be used for immune modulation. The utility of the compounds to treat inflammatory and serine protease mediated disorders can be determined according to the procedures described herein.

An embodiment of the invention is a method for treating inflammatory and serine protease mediated disorders in a subject in need thereof which comprises administering to the subject a therapeutically effective amount of any of the compounds or compositions described above. Also included in the invention is the use of a compound of Formula (I) for the preparation of a medicament for treating an inflammatory or serine protease mediated disorder in a subject in need thereof. The term "treating" as used herein refers to a method for improving, halting, retarding or palliating an inflammatory or serine protease mediated disorder in the subject in need thereof. All such methods of treatment are intended to be within the scope of the present invention.

In accordance with the methods of the present invention, the individual components of the compositions described herein can also be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal (preferably, a mammal; most preferably, a human) who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare the compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a composition of the present invention in liquid dosage form for oral, topical, inhalation/insufflation and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid compositions such as tablets, the principal active ingredient is mixed with a pharmaceutical carrier, e.g. conventional tabletting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to accacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate, cellulose acetate phthalate, polyvinyl acetate phthalate, hydroxypropyl methylcellulose phthalate, hydroxypropyl methylcellulose acetate succinate, methacrylate and ethylacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, aftapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in a form suitable for intranasal or inhalation therapy. For such therapy, compounds of the present invention are conveniently delivered in the form of a solution or suspension from a pump spray container that is squeezed or pumped or as an aerosol spray from a pressurized container or a nebulizer (such as, a metered dose inhaler, a dry powder inhaler or other conventional or non-conventional modes or devices for inhalation delivery) using a suitable propellant (such as, dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (such as, those made from gelatin) for use in an inhaler or insufflator may be formulated containing a powder mix of a compound of the invention and a suitable powder base such as lactose or starch.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

The therapeutically effective amount of a compound or composition thereof may be from about 0.001 mg/Kg/dose to about 300 mg/Kg/dose. Preferably, the therapeutically effective amount may be from about 0.001 mg/Kg/dose to about 100 mg/Kg/dose. More preferably, the therapeutically effective amount may be from about 0.001 mg/Kg/dose to about 50 mg/Kg/dose. Most preferably, the therapeutically effective amount may be from about 0.001 mg/Kg/dose to about 30 mg/Kg/dose. Therefore, the therapeutically effective amount of the active ingredient contained per dosage unit (e.g., tablet, capsule, powder, injection, suppository, teaspoonful and the like) as described herein will be in the range of from about 1 mg/day to about 21,000 mg/day for a subject, for example, having an average weight of 70 Kg. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. Advantageously, compounds of the present invention may be administered in a single daily dose or the total daily dosage may be administered in divided doses of two, three or four times daily.

Representative IUPAC names for the compounds of the present invention were derived using the ACD/LABS SOFTWARE™ Index Name Pro Version 4.5 nomenclature software program provided by Advanced Chemistry Development, Inc., Toronto, Ontario, Canada.

Abbreviations used in the instant specification, particularly the Schemes and Examples, are as follows:
Boc=tert-butoxycarbonyl
BuLi=n-butyllithium
Cpd=compound
DCC=dicyclohexylcarbodiimide
h=hour/hours
HOBT=hydroxybenzotriazole
KH=potassium hydride
MeI=methyliodide
NT=not tested
rt/RT=room temperature
TFA=trifluoroacetic acid
TMSBr=bromotrimethylsilane General Synthetic Methods Representative compounds of the present invention can be synthesized in accordance with the general synthetic methods described below and are illustrated more particularly in the scheme that follows. Since the scheme is an illustration, the invention should not be construed as being limited by the chemical reactions and conditions expressed. The preparation of the various starting materials used in the schemes is well within the skill of persons versed in the art.

Scheme A

Scheme A is illustrative of a general method for the preparation of compounds of the invention by addition of a phosphonate or phosphinate anion, prepared from a phosphonate or phosphinate Compound A2, and an organometallic base such as n-butyllithium, to an anhydride Compound A1 in a solvent such as THF to afford a ketophosphonate or ketophosphinate Compound A3, wherein Z is hydrogen, Y is not present and X is one oxygen substituent attached by a double-bond to the carbon in the position β to $R_4$.

Other compounds of the present invention may be obtained from Compound A3 using standard ketone manipulations wherein the β position carbon may be reduced from the ketone to a compound of Formula (I) wherein X and Y are both present or wherein Z is a bond. Examples of ketone manipulations include, but are not limited to, the use of 1) organometallic reagents to form alkoxy groups; 2) hydroxylamines to form imino groups; and, 3) Lawesson's reagent to substitute a thio group in place of the ketone (with appropriate protecting groups added to the COOH group shown).

Compound A2, wherein $R_6$ is as previously defined, can be made according to known methods, such as those described in Katritsky, et. al., *Org. Prep. Proced. Int.*, 1990, 22(2), 209-213; *J. Am. Chem. Soc.*, 2002, 124, 9386-9387; and, *Chem. Ber.*, 1963, 96, 3184-3194. In an embodiment of a general synthetic method, the $R_5$ substitutent of Compound A4 is hydrogen and the $R_6$ substitutent is ethoxy.

Compound A2, wherein $R_4$ is heteroaryl, can be prepared from commercially available or known haloalkyl substituted heteroaryl starting materials (such as 3-bromomethyl-5-Cl-benzothiophene used to prepare Cpd 33) using techniques known to those skilled in the art.

Compound A3 may be coupled to the $R_1$ portion of Formula (I) using standard coupling reactions. For example, when $R_1$ is a secondary amine in a heterocyclyl ring, the nitrogen on the ring may be coupled to Compound A3 (similar to the reaction shown in Scheme A, e.g. the ring nitrogen in Compound A4 would be coupled with Compound A8). Appropriate blocking groups can be employed to minimize undesirable side reactions. Analogous coupling reactions with Compound A3 can be performed when $R_1$ is $N(R_7R_8)$ to couple the substituted amine to the carboxylic acid of Compound A3. In one embodiment of the present invention the coupling reaction of Compound A3 with $R_1$ when $R_1$ is $N(R_7R_8)$ and $R_8$ is a heterocycle is provided to further illustrate the present invention.

In Scheme A, the reaction of a suitably protected amino substituted heterocycle Compound A4 (wherein the protected amino is substitusted with a hydrogen atom for $R_7$ and an unsubstituted ad). heterocycle for $R_8$) with a Q-substituted $R_{8a}$ Compound A5 (wherein Q is a suitable leaving group (such as, but not limited to, a halogen atom) and $R_{8a}$ is a substituent as previously defined in the $R_8$ ba).-bl) list) in a solvent such as DMF containing a base (such as, but not limited to, triethylamine) provided an $R_{8b}$ substituted Compound A6.

In an embodiment of a general synthetic method, the heterocyclyl portion of Compound A4 was further substituted on a nitrogen ring atom by reaction with an acid chloride Compound A5, wherein the Q portion was chlorine and wherein the $R_{8a}$ portion was bc). carbonyl substituted with an $R_{8b}$ substituent selected from $C_{1-8}$alkyl, aryl, aryl($C_{1-8}$)alkyl, aryl($C_{2-8}$)alkenyl, heteroaryl, heteroaryl($C_{1-8}$)alkyl or heteroaryl($C_{2-8}$)alkenyl. In an alternate embodiment, the reaction may performed by reaction with an acid chloride Compound A5, wherein the Q portion is chlorine and wherein the $R_{8a}$ portion is bl). sulfonyl substituted with an $R_{8b}$ substituent; wherein $R_{8b}$ is as previously defined.

Treatment of Compound A6 with a base such as potassium hydride followed by treatment with an $R_7X$ alkylating agent such as iodomethane in a solvent such as THF yielded Compound A7. The amine Compound A8 can be obtained from Compound A7 by removal of the Boc protecting group upon treatment with an acid such as TFA in a solvent such as $CH_2Cl_2$. The free base of Compound A8 is obtained upon treatment with a base such as aqueous $Na_2CO_3$.

Compound A9 can be prepared by a standard coupling procedure between Compound A3 and Compound A8 using routine reagents such as DCC and HOBT in a solvent such as $CH_3CN$. Dealkylation of Compound A9 with reagent such as bromotrimethylsilane in a solvent such as pyridine, followed by treatment with dilute HCl afforded Compound A10 (wherein, in an embodiment of a general synthetic method, the $R_5$ ethyl group and the $R_6$ ethoxy group were replaced with hydrogen). A salt of Compound A10 such as target Compound A11 can be prepared by treating Compound A10 with a monobasic or dibasic amine such as tris(hydroxymethyl)aminomethane in a solvent system such as i-PrOH and water.

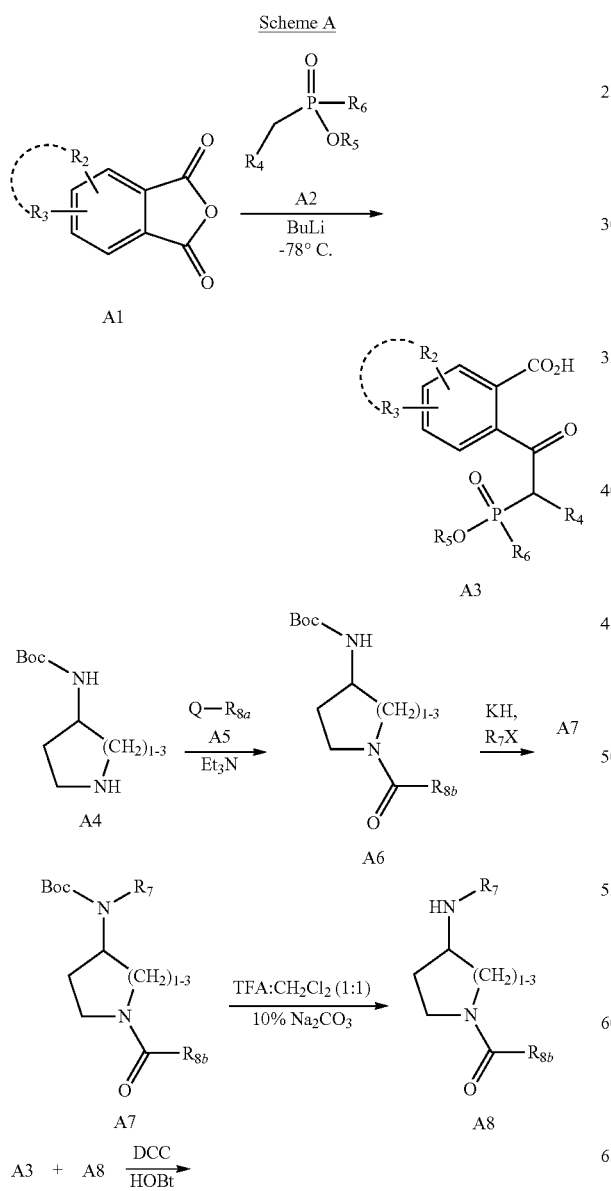

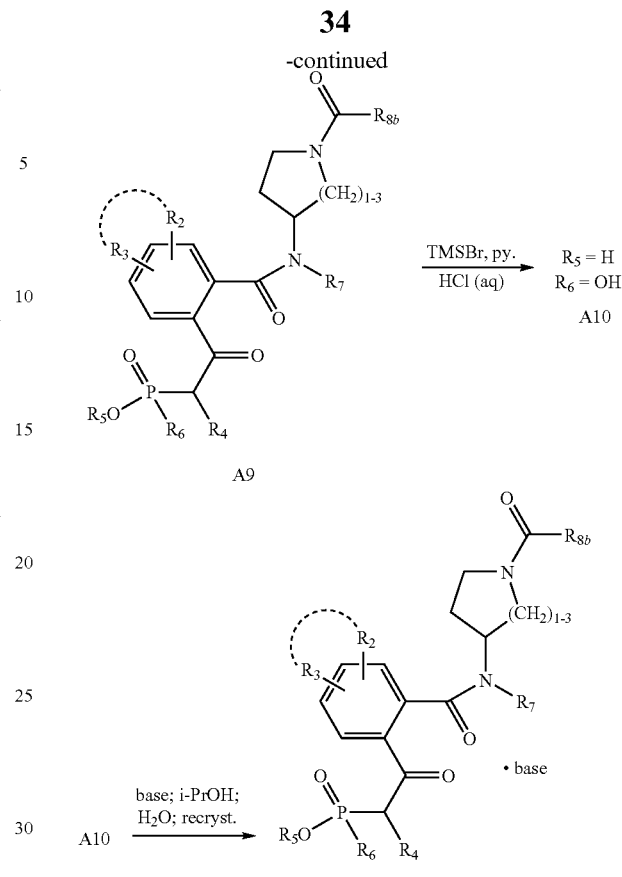

Scheme B

Scheme B is illustrative of an alternative general synthetic method for the preparation of compounds of the invention by addition of a Compound A2 (in an embodiment of an alternative general method, the $R_5$ substituent of Compound A2 is ethyl and the $R_6$ substituent is ethoxy) and R"M (wherein R"M represents an organometallic reagent such as LiHMDS (lithium hexamethyldisilylazide), lithium tetramethylpiperidide or NaHMDS (sodium hexamethyldisilazide)) to an anhydride Compound A1.

The reaction is subsequently quenched with 6N HCl to a pH between 4 and 6 to afford an enol Compound B1, wherein for a compound of Formula (I), Z is a bond, Y is not present and X is one oxygen substituent attached by a single-bond to the carbon in the position β to $R_4$. Other compounds of the present invention may be obtained from Compound B1 using standard ketone manipulation wherein the enol double bond may be reduced to the ketone; wherein for a compound of Formula (I), Y is not present and X is one oxygen substituent attached by a double-bond on the β position carbon. A coupling reagent (such as, but not limited to, chloroformates (such as, but not limited to, isobutyl chloroformate), cyanuric chloride, methanesulfonyl chloride, or diethyl chlorophosphate) may then be employed for ring closure to form a substituted lactone intermediate Compound B2 in the presence of a base such as, but not limited to, $Et_3N$.

Reaction of a dihydroxy substituted heterocycle Compound B3 (or other ketones and other protected ketones) with a Q-substituted $R_{8a}$ Compound A5 in a solvent (such as, but not limited to, $CH_2Cl_2$, THF or mixtures thereof) containing a base (such as, but not limited to, sodium bicarbonate, potassium carbonate) provided an $R_{8b}$ substituted Compound B4.

Compound B4 was treated with $R_7NH_2$ in a solvent (such as, but not limited to, $CH_2Cl_2$, THF or mixtures thereof) then subjected to reductive amination or hydrogenation using a hydride reducing agent (such as, but not limited to, NaBH(OAc)$_3$, or hydrogenation with Pd, Pt or Ni catalyst). The free base of Compound A8 was obtained upon quenching the reaction with a base such as aqueous $Na_2CO_3$.

Compound A9 (in tautomeric equilibrium with Compound B6) was prepared by opening the 5-membered lactone ring intermediate Compound B2 with Compound A8 (or Compound B5, a salt of Compound A8) in the presence of DIEA (diisopropylethylamine) in a solvent (such as, but not limited to, acetone or MEK (methylethyl ketone)).

Dealkylation of the equilibrium mixture of Compound A9-Compound B6 with a reagent (such as, but not limited to, TMSBr (bromotrimethylsilane) or TMSI) in a solvent (such as, but not limited to, $CH_3CN$ or pyridine), followed by recrystallization afforded Compound A10 (wherein the $R_5$ ethyl group is replaced with hydrogen and the $R_6$ ethoxy group is replaced with hydroxy). A salt of Compound A10 such as Compound A11 (and tautomers thereof) was prepared by treating Compound A10 with a diamine such as tris(hydroxymethyl)aminomethane in a solvent system such as a mixture of EtOH and water.

Scheme B

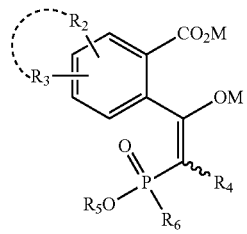

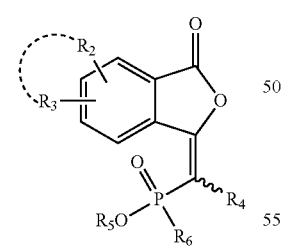

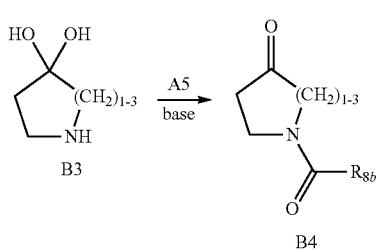

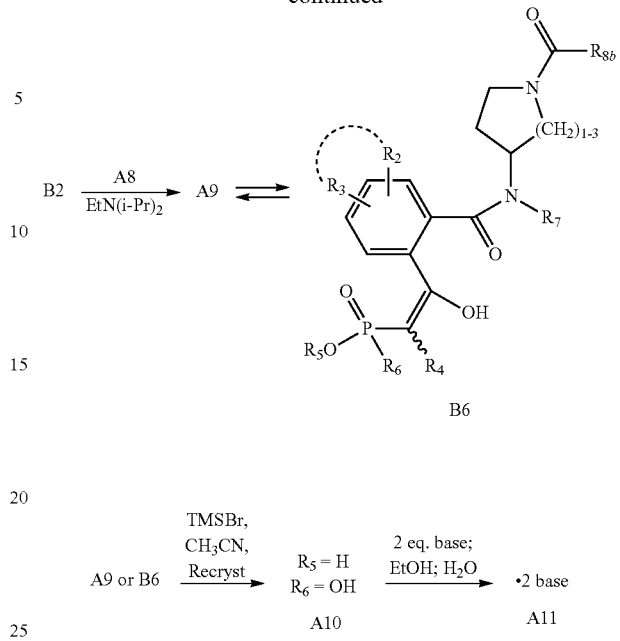

Scheme C

Scheme C is illustrative of an alternative method for the preparation of the intermediate Compound B2, wherein the enol Compound B1 is protonated to the free acid ketone Compound A3 by adjusting the pH to about pH 1, followed by intramolecular dehydration to provide the target lactone intermediate Compound B2.

Scheme C

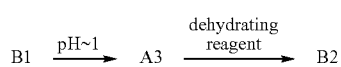

Scheme D

Scheme D is illustrative of a method for the preparation of an acid addition compound B5, wherein Compound A8 is reacted with an acid HA (such as, but not limited to, HCl, HBr or p-toluenesulfonic acid) to provide the target Compound B5 which may be carried forward in place of Compound A8 in the reaction with Compound B2.

Scheme D

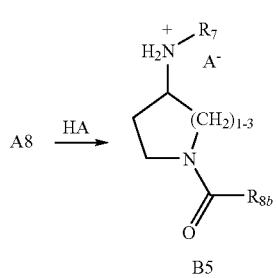

Scheme E

Scheme E is illustrative of a method of the preparation of compounds of Formula (II).

Compound A3 may be reacted with a compound of E1 under appropriate conditions to couple the compounds via an amide linkage. For example a salt can be formed from E1 and reacted with A3 to form an ammonium salt of the carboxylic acid that can be dehydrated to form the amide linkage.

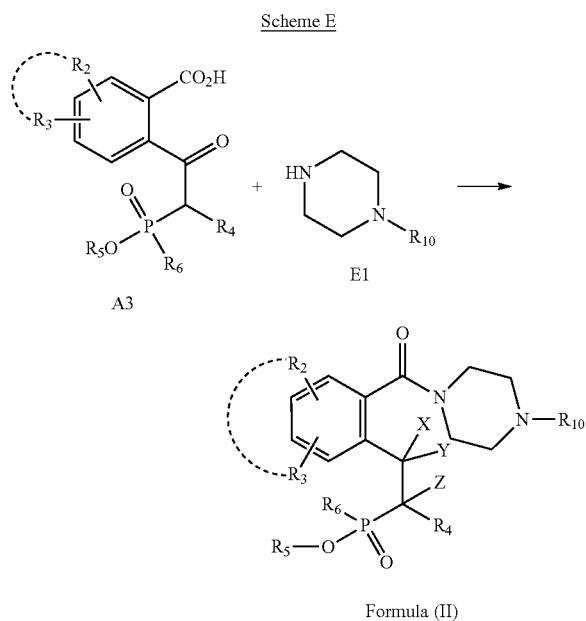

Scheme E

Formula (II)

Compound E1 can be prepared from commercially available or known starting materials using techniques known to those of skill in the art.

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. These reactions can be further optimized to increase the yields. One skilled in the art would know how to increase such yields through routine variations in reaction times, temperatures, solvents and/or reagents.

All chemicals were obtained from commercial suppliers and used without further purification. $^1$H and $^{13}$C NMR spectra were recorded on a Bruker AC 300B (300 MHz proton) or a Bruker AM-400 (400 MHz proton) spectrometer with Me$_4$Si as an internal standard (s=singlet, d=doublet, t=triplet, br=broad). APCI-MS and ES-MS were recorded on a VG Platform II mass spectrometer.

Example 1

[2-[3-[[methyl[1-(2-naphthalenylcarbonyl)-4-piperidinyl]amino]carbonyl]-2-naphthalenyl]-1-(1-naphthalenyl)-2-oxoethyl]-phosphonic Acid (Compound 2)

To a solution of 2.5M n-BuLi in hexanes (40 mL, 0.1 mol) in 70 mL of THF at −78° C. was added dropwise a solution of 1-naphthyldiethylphosphonate (Compound 1A, 28 g, 0.1 mol) in 60 mL THF over 30 min. After stirring for an additional 30 min, 2,3-naphthalenedicarboxylic anhydride (Compound 1B, 20 g, 0.1 mol) was added portionwise via solid-addition funnel to the mixture over 20 min. After the addition was complete, the slurry was allowed to reach 0° C. gradually where it was held for another 1.5 h. Excess NH$_4$Cl (sat'd., aq.) was added, and the mixture was filtered through a pad of Celite 545. The filtrate was extracted with 200 mL of EtOAc and the layers were separated. The organic phase was concentrated (without drying) under reduced pressure at rt and the residue was triturated 4× with boiling ether. The residue was treated with 200 mL of EtOAc and adjusted to pH 3 with 2N HCl (aq.) with vigorous stirring. The layers were separated, and the organic phase was washed once with H$_2$O, dried (Na$_2$SO$_4$) and concentrated to afford 24 g of Compound 1C as a white powder: MS (ES) MH+=477; HPLC: 3.68 min.

To a solution of Compound 1D (4 g, 20 mmol) containing 3.1 mL of triethylamine (22 mmol) in 45 mL of DMF was added Compound 1E (3.8 g, 20 mmol). After stirring overnight, the mixture was filtered and concentrated under reduced pressure. The residue was taken up in CH$_2$Cl$_2$ and washed sequentially with H$_2$O, Na$_2$CO$_3$ (10%, aq.), H$_2$O, KHSO$_4$ (1N aq.) and H$_2$O. The organic phase was dried (Na$_2$SO$_4$), and concentrated to afford 6.0 g of Compound 1F as a foam: MS (ES) MH$^+$=355.

Potassium hydride (2.3 g of a 35% oil dispersion; 20 mmol) was washed with hexanes, then treated with 30 mL of THF and cooled to 0° C. To the suspension was added dropwise a solution of Compound 1F (5.9 g, 16.8 mmol) in 15 mL of THF. The mixture was stirred at 0° C. for 0.5 h, then stirred an additional 0.5 h at rt. The mixture was cooled to 0° C. and iodomethane (15.7 g, 100 mmol) was added dropwise. The mixture was stirred at 0° C. for 0.5 h then warmed to rt and stirred an additional 1.5 h. Excess 10% Na$_2$CO$_3$ (aq) was added slowly at 0° C., and the volatiles were removed under reduced pressure. The aqueous layer was extracted 3 times with EtOAc and the combined extracts were dried (Na$_2$SO$_4$) and concentrated to yield 6.1 g of Compound 1G as foam. HPLC R$_t$=3.76 min, 100%; MS (ES) MH+=369.

A solution of Compound 1G (6.1 g, 16.5 mmol) was dissolved in 15 mL of a 1:1 solution of TFA:CH$_2$Cl$_2$ and stirred for 1 h at rt. Volatiles were removed under reduced pressure, and the residue was dissolved in CH$_2$Cl$_2$ and treated with excess 10% Na$_2$CO$_3$ (aq). The layers were separated, and the aqueous phase was extracted 3 times with CH$_2$Cl$_2$. The organic extracts were combined, dried (Na$_2$SO$_4$) and concentrated to afford 4.3 g of Compound 1H as a viscous oil. HPLC R$_t$=1.5 min, 100%; MS (ES) MH$^+$=269.

A solution of Compound 1C (4.9 g, 10.3 mmol), Compound 1H (3.3 g, 12.3 mmol) and HOBT (2.1 g, 15.4 mmol) in 100 mL CH$_3$CN was treated with a solution of DCC (2.5 g, 12.3 mmol) in 7 mL of CH$_3$CN. After stirring for 12 h, 5 mL of DIPEA was added and the reaction was stirred for an additional 48 h. The mixture was filtered and concentrated. The residue was purified by flash column chromatography (silica: CH$_2$Cl$_2$:MeOH ramped from 98:1 to 95:5) to yield 6.9 g of Compound 1I. HPLC R$_t$=4.3 min; MS (ES) MH$^+$=727.

To a solution of Compound 1I in 15 mL of pyridine was added 5 mL of bromotrimethylsilane. The mixture was stirred for 15 min, then concentrated under reduced pressure. The residue was treated with excess 3N HCl(aq), then stirred for 3 h. The white precipitate was collected and rinsed with water, then triturated with CH$_3$CN to afford 5.1 g of Compound 1J. HPLC R$_t$=3.6 min; MS (ES) MH+=671. To a solution of Compound 1J in 50 mL of CH$_3$CN was added a solution of tris(hydroxymethyl)aminomethane (0.9 g, 7.7 mmol) in 7 mL of H$_2$O. The solution was filtered and the filtrate lyophilized after partial concentration to remove most of the CH$_3$CN. The resulting white solid was recrystallized from i-PrOH to yield 5.5 g of Compound 2 as an off-white solid. HPLC: R$_t$=3.6 min; 100%; MS (ES) MH+=671; Anal. Calc'd for C$_{40}$H$_{35}$N$_2$O$_6$P.1.0 C$_4$H$_{11}$NO$_3$.1.0 i-PrOH-1.5H$_2$O: C, 64.23; H, 6.54; N, 4.79; H$_2$O, 3.08. Found: C, 63.93; H, 6.40; N, 4.85; H$_2$O, 2.74.

For Example 1, TLC was performed using Whatman 250-μm silica gel plates. Preparative TLC was performed with Analtech 1000-μm silica gel GF plates. Flash column chromatography was conducted with flash column silica gel (40-63 μm) and column chromatography was conducted with standard silica gel. HPLC separations were carried out on three Waters PrepPak® Cartridges (25×100 mm, Bondapak® C18, 15-20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

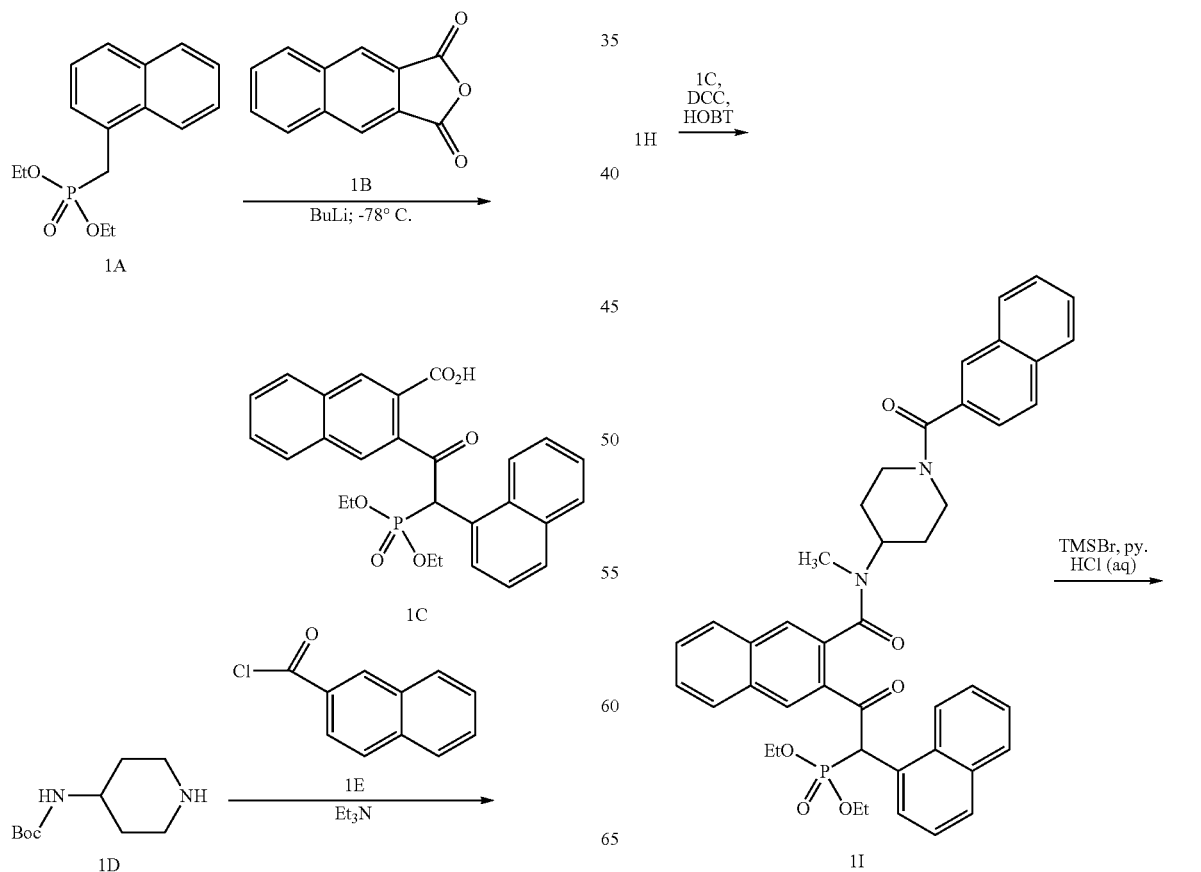

41
-continued

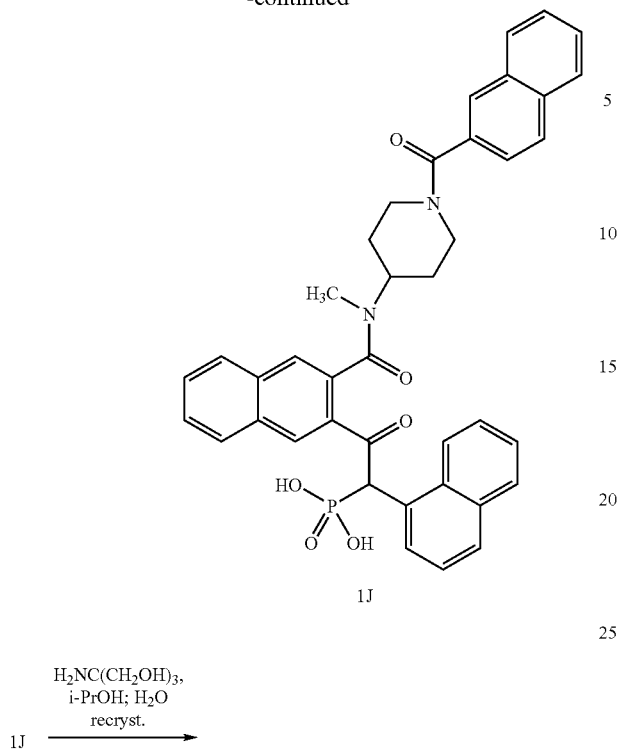

1J

H₂NC(CH₂OH)₃,
i-PrOH; H₂O
recryst.

1J ⟶

42
-continued

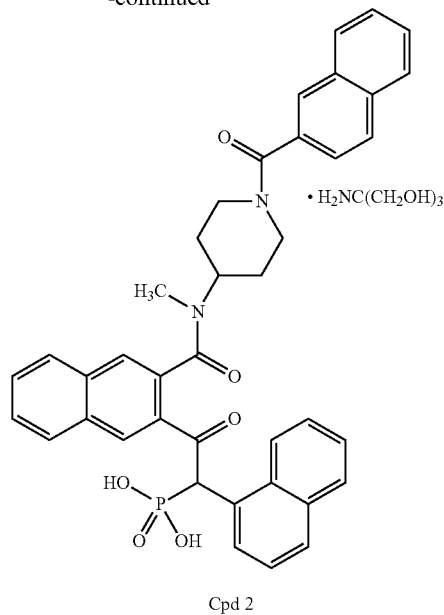

Cpd 2

Following the procedure of Example 1 and substituting the appropriate starting materials, compounds and reagents, the following Compounds 1 and 3-33 of the invention were also prepared:

| Cpd | Name | MS m/e (MH⁺). |
|---|---|---|
| (1) | [2-[3-[[methyl(4-phenylcyclohexyl)amino]carbonyl]-2-naphthalenyl]-1-(1-naphthalenyl)-2-oxoethyl]-phosphonic acid | 592 |
| (3) | [2-[3-[[[1-[(6-methoxy-2-naphthalenyl)carbonyl]-3-pyrrolidinyl]methylamino]carbonyl]-2-naphthalenyl]-1-(1-naphthalenyl)-2-oxoethyl]-phosphonic acid | 687 |
| (4) | [2-[3-[[[1-[(6-bromo-2-naphthalenyl)carbonyl]-4-piperidinyl]methylamino]carbonyl]-2-naphthalenyl]-1-(1-naphthalenyl)-2-oxoethyl]-phosphonic acid | 771 ($M^{+Na}$) |
| (5) | [2-[3-[[[1-[(2E)-3-(4-fluorophenyl)-1-oxo-2-propenyl]-3-pyrrolidinyl]methylamino]carbonyl]-2-naphthalenyl]-1-(1-naphthalenyl)-2-oxoethyl]-phosphonic acid | 651 |
| (6) | [2-[3-[[methyl[1-[(2E)-1-oxo-3-phenyl-2-propenyl]-4-piperidinyl]amino]carbonyl]-2-naphthalenyl]-1-(1-naphthalenyl)-2-oxoethyl]-phosphonic acid | 647 |
| (7) | [1-(1-naphthalenyl)-2-oxo-2-[3-[[(4-phenyl-1-piperidinyl)carbonyl]-2-naphthalenyl]ethyl]-phosphonic acid | 564 |
| (8) | [1-(1-naphthalenyl)-2-oxo-2-[3-[(4-oxo-1-phenyl-1,3,8-triazaspiro[4.5]dec-8-yl)carbonyl]-2-naphthalenyl]ethyl]-phosphonic acid | 634 |
| (9) | [2-[3-[[methyl[1-[(2E)-3-(4-methylphenyl)-1-oxo-2-propenyl]-4-piperidinyl]amino]carbonyl]-2-naphthalenyl]-1-(1-naphthalenyl)-2-oxoethyl]-phosphonic acid | 661 |
| (10) | [2-[3-[[methyl[1-[(2E)-1-oxo-3-[4-(trifluoromethyl)phenyl]-2-propenyl]-4-piperidinyl]amino]carbonyl]-2-naphthalenyl]-1-(1-naphthalenyl)-2-oxoethyl]-phosphonic acid | 715 |
| (11) | [2-[3-[[methyl[1-(2-naphthalenylcarbonyl)-4-piperidinyl]amino]carbonyl]-2-naphthalenyl]-2-oxo-1-phenylethyl]-phosphonic acid | 621 |
| (12) | [2-[3-[[4-(4-methoxyphenyl)-1-piperidinyl]carbonyl]-2-naphthalenyl]-1-(1-naphthalenyl)-2-oxoethyl]-phosphonic acid | 594 |
| (13) | [2-[3-[[[1-[(2E)-3-[4-(dimethylamino)phenyl]-1-oxo-2-propenyl]-4-piperidinyl]methylamino]carbonyl]-2-naphthalenyl]-1-(1-naphthalenyl)-2-oxoethyl]-phosphonic acid | 690 |
| (14) | [2-[3-[[4-(3-methoxyphenyl)-1-piperidinyl]carbonyl]-2-naphthalenyl]-1-(1-naphthalenyl)-2-oxoethyl]-phosphonic acid | 594 |

| Cpd | Name | MS m/e (MH+). |
|---|---|---|
| (15) | [2-[3-[[(1-benzoyl-4-piperidinyl)methylamino]carbonyl]-2-naphthalenyl]-1-(1-naphthalenyl)-2-oxoethyl]-phosphonic acid | 621 |
| (16) | [2-[3-[[4-(2-benzothiazolyl)-1-piperidinyl]carbonyl]-2-naphthalenyl]-1-(1-naphthalenyl)-2-oxoethyl]-phosphonic acid | 621 |
| (17) | [2-[3-[(cyclohexylmethylamino)carbonyl]-2-naphthalenyl]-1-(1-naphthalenyl)-2-oxoethyl]-phosphonic acid | 516 |
| (18) | [2-[3-[[methyl[1-[1-oxo-3-[4-(trifluoromethyl)phenyl]propyl]-4-piperidinyl]amino]carbonyl]-2-naphthalenyl]-1-(1-naphthalenyl)-2-oxoethyl]-phosphonic acid | 717 |
| (19) | [1-(1-naphthalenyl)-2-oxo-2-[3-[(3-phenyl-1-pyrrolidinyl)carbonyl]-2-naphthalenyl]ethyl]-phosphonic acid | 550 |
| (20) | [2-[3-[[methyl[1-(2-methyl-1-oxopropyl)-4-piperidinyl]amino]carbonyl]-2-naphthalenyl]-1-(1-naphthalenyl)-2-oxoethyl]-phosphonic acid | 587 |
| (21) | [2-[3-[(cyclopentylmethylamino)carbonyl]-2-naphthalenyl]-1-(1-naphthalenyl)-2-oxoethyl]-phosphonic acid | 502 |
| (22) | [2-[3-[[[4-(1,1-dimethylethyl)cyclohexyl]methylamino]carbonyl]-2-naphthalenyl]-1-(1-naphthalenyl)-2-oxoethyl]-phosphonic acid | 572 |
| (23) | [2-[3-[[methyl[1-(2-naphthalenylcarbonyl)-4-piperidinyl]amino]carbonyl]-2-naphthalenyl]-1-(1-naphthalenyl)-2-oxoethyl]-phosphonic acid methyl ester | 685 |
| (24) | [2-[3-[[[1-[(6-hydroxy-2-naphthalenyl)carbonyl]-4-piperidinyl]methylamino]carbonyl]-2-naphthalenyl]-1-(1-naphthalenyl)-2-oxoethyl]-phosphonic acid | 687 |
| (25) | [1-(1-naphthalenyl)-2-oxo-2-[3-[[3-(2-phenylethyl)-1-pyrrolidinyl]carbonyl]-2-naphthalenyl]ethyl]-phosphonic acid | 578 |
| (26) | [2-[3-[[(1-acetyl-4-piperidinyl)methylamino]carbonyl]-2-naphthalenyl]-1-(1-naphthalenyl)-2-oxoethyl]-phosphonic acid | 559 |
| (27) | [2-[3-[[methyl(4-methylcyclohexyl)amino]carbonyl]-2-naphthalenyl]-1-(1-naphthalenyl)-2-oxoethyl]-phosphonic acid | 530 |
| (28) | [2-[1-[[methyl(tricyclo[3.3.1.1$^{3,7}$]dec-1-ylmethyl)amino]carbonyl]-2-naphthalenyl]-1-(1-naphthalenyl)-2-oxoethyl]-phosphonic acid | 582 |
| (29) | [2-[3-[[methyl(4-phenyl-3-cyclohexen-1-yl)amino]carbonyl]-2-naphthalenyl]-1-(1-naphthalenyl)-2-oxoethyl]-phosphonic acid | 590 |
| (30) | [1-(1-naphthalenyl)-2-[3-[[[1-(2-naphthalenylcarbonyl)-4-piperidinyl]amino]carbonyl]-2-naphthalenyl]-2-oxoethyl]-phosphonic acid | 657 |
| (31) | [2-[2-[[methyl[1-(2-naphthalenylcarbonyl)-4-piperidinyl]amino]carbonyl]phenyl]-1-(1-naphthalenyl)-2-oxoethyl]-phosphonic acid | 621 |
| (32) | methyl[2-[3-[[methyl[1-(2-naphthalenylcarbonyl)-4-piperidinyl]amino]carbonyl]-2-naphthalenyl]-1-(1-naphthalenyl)-2-oxoethyl]-phosphinic acid | 669 |
| (33) | [1-(5-chlorobenzo[b]thien-3-yl)-2-[3-[[methyl[1-(2-naphthalenylcarbonyl)-4-piperidinyl]amino]carbonyl]-2-naphthalenyl]-2-oxoethyl]-phosphonic acid | 712 |

Example 2

Alternative Method of Synthesis for Compound 2

THF (tetrahydrofuran) (1081.0 mL) and 1-naphthyldiethylphosphonate Compound 2B (223.0 gm, 0.7612 mol) were combined in a flask and cooled to about −20° C. using a dry ice-methanol cooling bath. A solution of 1M LiHMDS (1597.0 mL, 1.597 mol) in THF was added to the cooled mixture while keeping the temperature at about −20° C. to form a fine slurry which was stirred for an additional 30 minutes. A 2,3-naphthalinedicarboxylic anhydride Compound 2A (158.80 gm, 0.7612 mol) was added portionwise over about a 1 h period while keeping the temperature of the mixture at about −20° C. The addition funnel and flask walls were rinsed with THF (100.0 mL), the cooling bath was removed and the mixture temperature raised to about 5° C. for about 1.5 h. Once the reaction was complete (as shown by HPLC), the final pH of the mixture was adjusted to about pH 5 by slowly adding 6N HCl (422 mL, 2.34 mol) while the temperature of the mixture was maintained at about 5° C. The mixture was stirred for about 30 min more at about 5° C. to provide a crude product as a fine white solid. The crude product was filtered using a porcelain filter. The wet solid was then washed with water (1000.0 mL), left to filter overnight, then dried at 70° C. to provide a dilithium salt Compound 2C (365.1 gms; mass yield: 100.6%). Compound 2C was used in the next step without further purification.

Methanol (2500.0 mL) and water (360.0 mL) were added to a flask and stirred. Compound 2C (365.1 gm, 0.7612 mol) was added to the stirring solution and the flask was rinsed with methanol (100.0 mL) to form a slurry. The slurry was stirred at RT for 30 minutes and then 12 N HCl (80.0 mL, 0.960 mol) was added over a 2 min period as the slurry turned into a hazy solution. The solution was stirred at RT until crystallization began, then was cooled to about 5° C. for 1 h to provide a crude product as a white granular solid. The product was filtered and washed with water (500.0 mL), then dried in vacuo overnight at a temperature of about 50° C. to provide Compound 2D (280 gms; mass yield: 77.3%).

Compound 2D (199.8 gm) and THF (2 L) were combined in a flask, then agitated and cooled to a temperature of from about 0° C. to about 5° C. NMM (4-methylmorpholine) (51.5 mL) was added to the flask while the mixture temperature was maintained at a temperature of from about 0° C. to about 5° C. The mixture was then agitated for an additional 15 min or until a solution was obtained. IBCF (isobutylchloroformate) (56 mL) was added portionwise while the mixture temperature was maintained at a temperature of from about 0° C. to about 15° C. When the addition was complete, the mixture temperature was warmed to a temperature of from about 20° C. to about 25° C., then agitated for 1 h. Once the reaction was complete, the NMM salts were filtered, washed with THF (150 mL) and allowed to dry. The filtrate was then combined with n-heptane (2.5 L) over a period of about 10 min and then agitated at a temperature of from about 20° C. to about 25° C. for about 30-45 min. Additional n-heptane (1.5 L) was added over a period of about 10 min. The mixture was then cooled to a temperature of from about 0° C. to about 5° C. and aged for about 1.5 h. The resulting suspension was filtered and washed with n-heptane (250 mL), allowed to air dry over a period of about 30 min and then dried in vacuo overnight at a temperature of from about 45 to about 50° C. to provide Compound 2E (165 gms; mass yield: 88.4%).

DCM (dichloromethane) (600 mL) and a 2-naphthoyl chloride Compound 2F (189.0 gm) were combined in a flask and agitated until solubilized. 4-Piperidone hydrate hydrochloride Compound 2G (150 g) and $NaHCO_3$ (sodium hydrogen carbonate) (260.0 gms) were then added via addition funnel. DCM (300 mL) was used to rinse the funnel and the resulting mixture was agitated for 18 h. Once the reaction was complete (as shown by HPLC), water (2.6 L) was added to the flask and the mixture was stirred vigorously to dissolve the $NaHCO_3$. After a period of about 5 to about 10 minutes, the layers were allowed to separate over a period of about 30 minutes. The aqueous layer was removed. Saturated aqueous $NaHCO_3$ (300 mL) was again added and the mixture agitated for a period of about 5 to about 10 min. The layers were allowed to separate over a period of about 30 min and the aqueous layer was removed. Water (300 mL) was added and the mixture stirred gently for a period of from about 5 to about 10 min. The layers were allowed to separate over a period of about 30 min and the organic layer (~960 mL) containing Compound 2H was removed (concentration of Compound 2H in DCM: 235.98 mg/mL; calculated mass of Compound 2H in DCM: 226.54 gms; calculated mass yield: 93.46%).

Compound 2H (~50 gms, ~265 mg/mL in DCM) and acetic acid (4.9 mL) were combined in a flask and the mixture was cooled to a temperature of from about 0° C. to about 5° C. 2.0M $MeNH_2$ (methylamine) (296 mL) in THF was added portionwise while maintaining the mixture at a temperature of from about 0° C. to about 19° C. The mixture was allowed to warm to ambient temperature and was agitated for a period of about 30 min. $NaBH(OAc)_3$ (sodium triacetoxyborohydride) (51.4 gms) was then added portionwise while maintaining the solution at a temperature of from about 19° C. to about 27° C. The mixture was aged for about 40 min at a temperature of from about ambient to about 27° C. Once the reaction was complete (as shown by HPLC), water (500 mL) was added while maintaining the solution at a temperature of below about 30° C. Sodium hydroxide (115 mL; 5% w/v in water) was then added to the mixture to raise the pH to from about pH 10 to about pH 11. The mixture was agitated vigorously for a period of from about 3 to about 10 min. The layers were separated and the aqueous layer was removed. Water (143 mL) was added and the mixture agitated for a period of from about 3 to about 10 min. The layers were again separated and the organic layer containing Compound 2I was removed (concentration of Compound 2I in DCM: 0.229 mg/mL; calculated mass of Compound 2I in DCM: 45.18 gms; mass yield: 85.3%).

Compound 2I (150 mL, 0.069 mol) was placed in solution with $CH_2Cl_2$:THF (150 mL; 1:8) and concentrated to a thick oil in vacuo while maintaining the mixture at a temperature of about or below 40° C. using a cooling bath. 2-Butanone (320 mL) was added portionwise to the thick oil to transfer the oil to another flask. The mixture was agitated and $EtN(i-Pr)_2$ (diisopropylethylamine) (11.0 mL, 0.063 mol) and Compound 2E (27.3 gms, 0.057 mol) were added. The mixture was heated to a temperature of about 65° C. for a period of from about 6 to about 7 h. Once the reaction was complete (as shown by HPLC), the mixture was cooled to ambient temperature and crystallized over a period of from about 72 to about 96 h (the product can take up to 48 h to start to crystallizing, having a cloud point time around 28 h). The product was filtered and washed with acetone (2×10 mL) (each wash), then dried in vacuo overnight at a temperature of about 75° C. to provide Compound 2J (31.4 gms; yield: 75.1%) as a white powder.

Compound 2J (10.0 g) and acetonitrile (40 mL) under nitrogen were added to a flask to form a suspension. The suspension was agitated for a period of from about 5 to about 10 min, then bromotrimethylsilane (10 mL) was added via additional funnel over a period of from about 10 to about 15 min at RT. The solution was stirred for at least a time period of about 1 h at rt. Once the reaction was complete (as shown by HPLC), the mixture was transferred to an addition funnel and then added to water (250 mL). The resulting slurry was stirred vigorously during the addition and the temperature maintained at from about 20° C. to about 25° C. The slurry was further agitated over a period of from about 1 to about 1.5 h, then filtered and washed with water (2×15 mL). The resulting wet cake was then dried in vacuo overnight at a temperature of about 40° C. to provide a crude product Compound 2K (10.2 gms) as a white solid.

Compound 2K (110.0 gms, 0.127 mol) and methanol (550 mL) were added to a flask to form a slurry. The slurry was stirred at RT over a period of from about 55 to about 60 min (the recrystallization mixture gave a hazy solution within about 5 minutes after adding MeOH and gradually afforded a white suspension after about 30 minutes). An acetone:water (1100 mL; 4:1) solution was added and the suspension was stirred at RT for a period of from about 180 to about 190 min to afford a white solid. The solid was filtered and washed with water (3×350 mL), forming a wet cake was then dried in vacuo overnight at a temperature of from about 30 to about 35° C. to provide a recrystallized Compound 2K (82.3 gms; yield: 96.1%) as a fine white solid.

Recrystallized Compound 2K (30.0 g, 0.0431 mol) and tris(hydroxymethyl)aminomethane (13.07 g, 0.107 mol; a clear white crystalline solid) were combined in a flask and ethanol (300 mL) and water (30 mL) were added. The solution was agitated to provide a clear solution after a period of about 15 min. A thin suspension was formed after a period of from about 2 to about 3 h and a thick white suspension was formed after a period of from about 3 to about 5 h (the mixture may need to be seeded to enhance crystallization if a thin suspension is not formed after a period of about 3 h). The suspension was stirred at RT for an additional period of about 4 h. The thick suspension was thinned by adding ethanol (180 mL), then filtered and washed with ethanol (120 mL), allowed to air dry over a period of about 30 min and then dried in vacuo for a time period of from about 24 to about 67 h at a temperature of about 40° C. to provide Compound 2E (38.6 gms; yield: 91.8%) as a bis-tromethane salt (ratio of tris(hydroxymethyl)aminomethane: Compound 2E: 1.99:1).

For Example 2, analytical HPLC was carried out using Phenomenex Luna (15 cm×4.6 mm; 5μ; detection was at 220 nm), Phenomenex Luna 5μ C18(2) (4.6 mm×250; detection was at 225 nm) and Synergi 4μ MAX-RP 80A (15 cm×4.6 mm; detection was at 225 nm) columns. Microanalysis was performed by Quantitative Technologies, Inc.

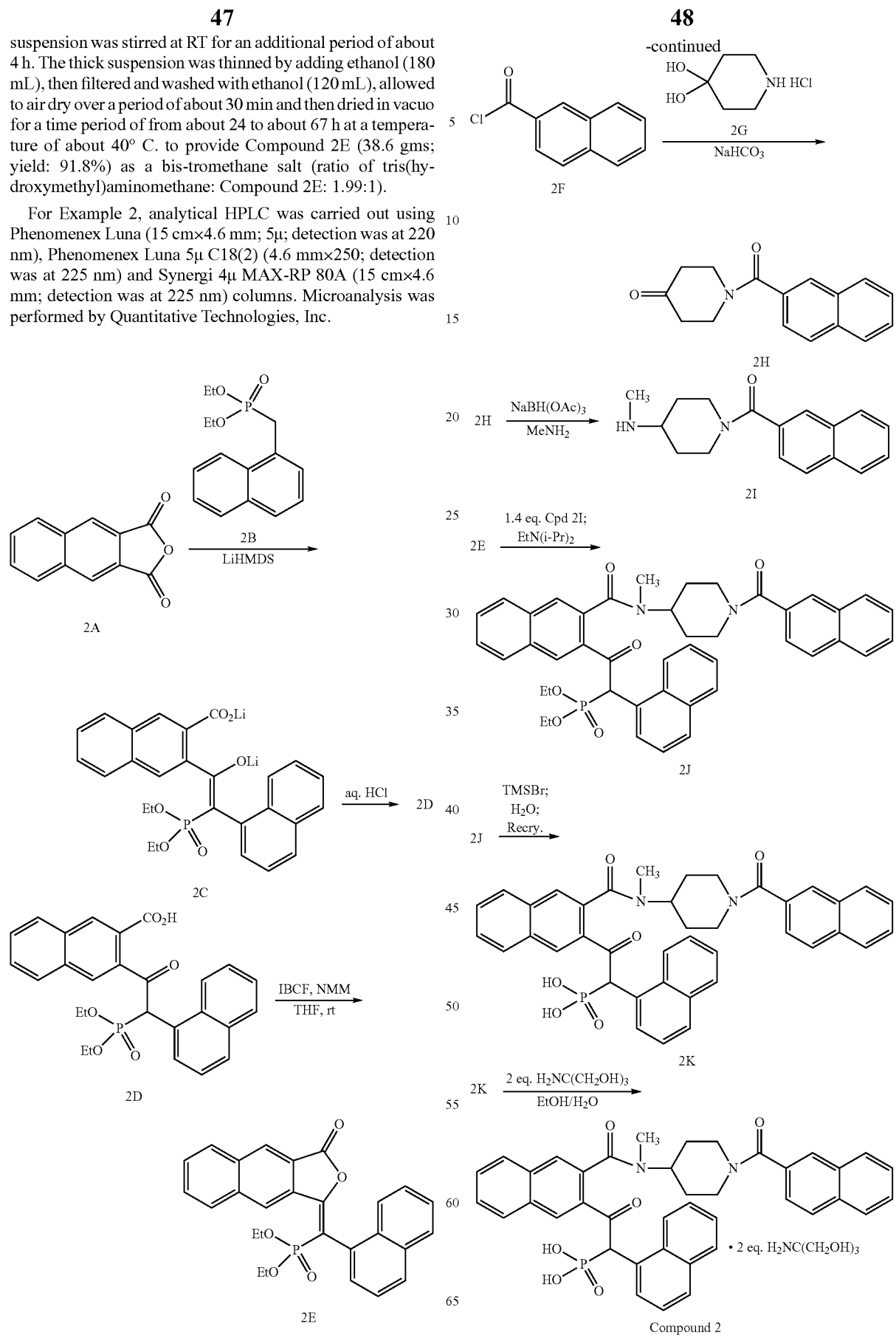

Example 3

As a specific embodiment of an oral composition, 100 mg of the Compound 2 of Example 1 is formulated with sufficient finely divided lactose to provide a total amount of 580 to 590 mg to fill a size 0 hard gel capsule.

Example 4

Compound 34

[2-(3-{4-[(Naphthalene-2-carbonyl)-amino]-piperidine-1-carbonyl}-naphthalen-2-yl)-1-naphthalen-1-yl-2-oxo-ethyl]-phosphonic acid A solution of 4A (1.0 g, 2.1 mmol), 4-N-Boc-aminopiperidine (0.42 g, 2.2 mmol; Astatech Inc.) and HOBt (0.28 g, 2.1 mmol) in 5 mL of DMF was treated with a solution of DCC (0.43 g, 2.1 mmol) in 1 mL of DMF dropwise. After stirring for 24 h, the mixture was filtered through dicalite and the filtrate concentrated under reduced pressure. The residue was purified by flash column chromatography (silica; 5% $CH_3OH$—$CH_2Cl_2$) to afford 1 g of 4B as a white foam, 72%. MS (ES) m/z 731 ($MH^+$ adduct ion with MeOH and $CH_3CN$).

A solution of 20% TFA in $CH_2Cl_2$ and 4B (1 g, 1.5 mmol) was stirred for 45 min, then concentrated under a stream of $N_2$. The residue was triturated with ether to give 0.80 g of C as a white powder (TFA salt): MS (ES) m/z=530 $(M-C_2H_5)^+$.

To a mixture of 0.40 g (0.59 mmol) of 4C and 0.17 mL (1.2 mmol) of $Et_3N$ in 30 mL of $CH_2Cl_2$ was added a solution of 2-naphthoyl chloride (0.11 g, 0.60 mmol) in 1 mL of $CH_2Cl_2$. The reaction was stirred for 2 h, then diluted with water and the layers were separated. The organic layer was washed sequentially with $H_2O$, $NaHCO_3$ (satd, aq.), 1N $KHSO_4$ (aq), and $H_2O$, then dried over $Na_2SO_4$, filtered and concentrated. The residue was purified by flash column chromatography (silica, 5% $CH_3OH$—$CH_2Cl_2$) to afford 0.29 g (70%) of 4D as a white powder: MS (ES) m/z 713 ($MH^+$).

A solution of 0.29 g (0.40 mmol) of 4D in 2.5 mL of pyridine was treated with 0.4 mL (3.3 mmol) of bromotrimethylsilane and the mixture was stirred for 2 h. Volatiles were removed under reduced pressure, and the white solid residue was treated with 15 mL of 1N HCl (aq). The slurry was stirred for 2.5 h and the white solid was collected and rinsed with $H_2O$. The solid was triturated with $CH_3CN$ to yield 0.12 g of the title compound (46%) as a white powder: MS (ES) m/z 657 ($MH^+$).

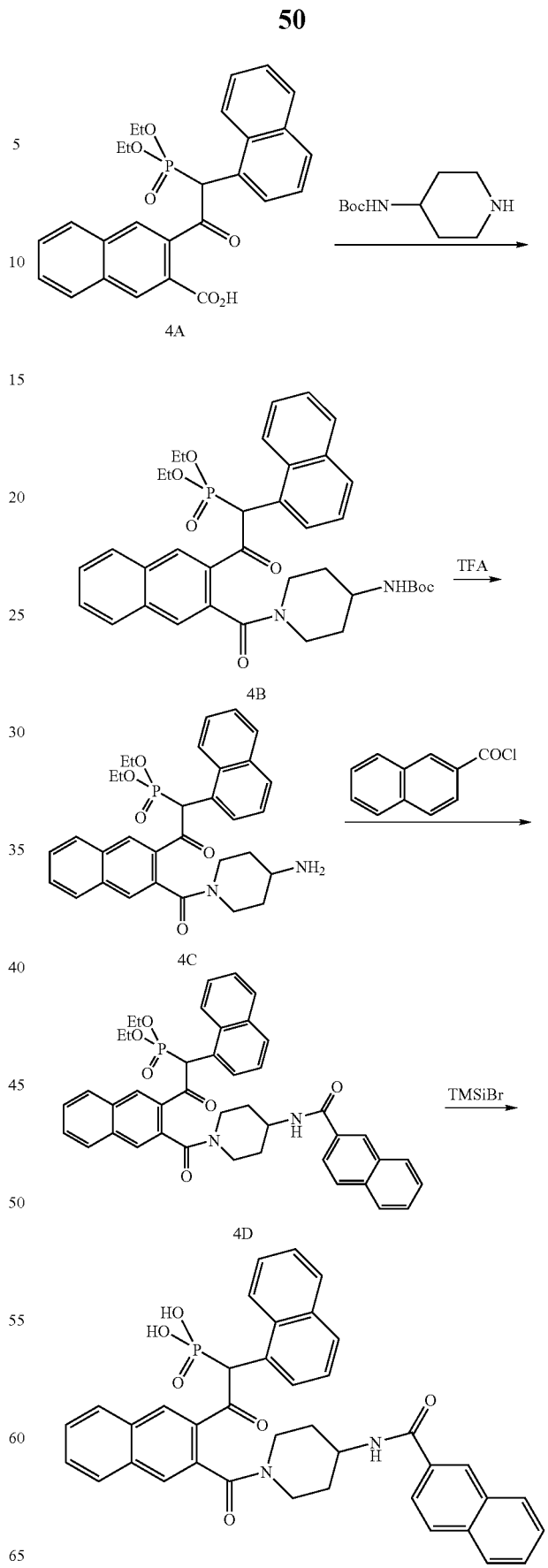

Example 5

Compound 35

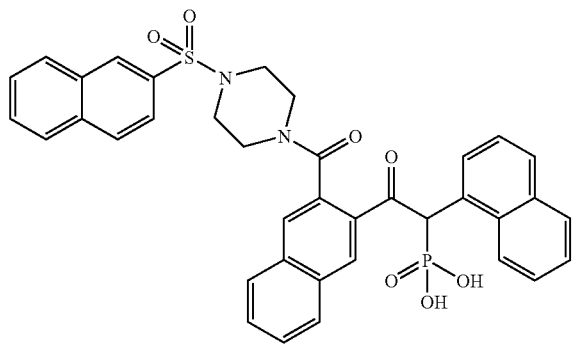

(2-{3-[4-(Naphthalene-2-sulfonyl)-piperazine-1-carbonyl]-naphthalen-2-yl}-1-naphthalen-1-yl-2-oxo-ethyl)-phosphonic acid To a stirred solution of 5A (0.55 g, 1.16 mmol), the trifluoroacetate salt of 5B (0.5 g, 1.16 mmol), triethylamine (1.28 mmol, 0.18 mL), and HOBt (0.24 g, 1.75 mmol) in 5 mL of acetonitrile was added a solution of DCC in 2 mL of acetonitrile. (0.26 g, 1.28 mmol). The reaction was stirred for 24 h, then treated with 1 mL of DIPEA, and stirred an additional 5 h. The mixture was filtered, and the filtrate was concentrated under reduced pressure. The residue was purified by flash column chromatography (silica; 100% $CH_2Cl_2$->98% $CH_2Cl_2$-MeOH) to afford 0.66 g of 5C as a foam: MS ($ES^+$) $MH^+$=735.

To a stirred solution of 5C (0.11 g, 0.75 mmol) in 1 mL of pyridine was added 0.15 mL of bromotrimethylsilane. The reaction was stirred for 1.5 h, then concentrated under reduced pressure. The residue was stirred with excess 3N HCl for 1 h, and the product collected and washed sequentially with water and ether. The product was suspended in acetonitrile and stirred for 0.5 h at 0° C. then collected to afford 0.067 g of the title compound as a white solid: MS ($ES^+$) $MH^+$=679.

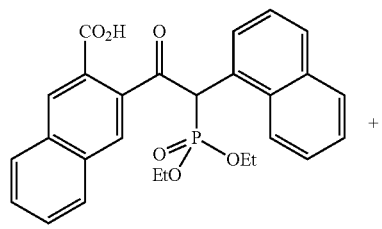

5A

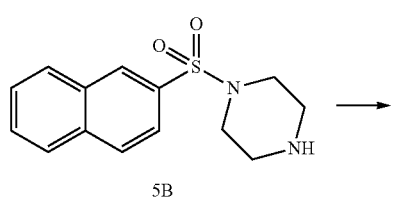

5B

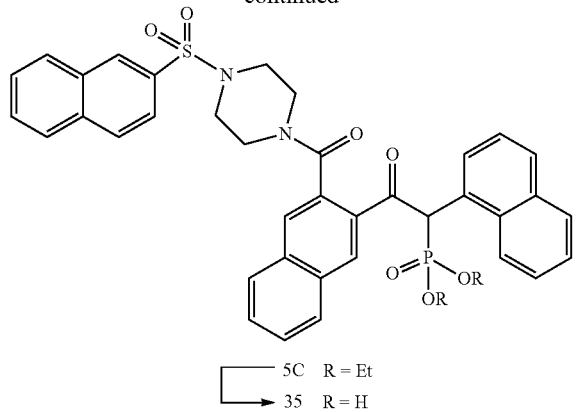

5C R = Et
35 R = H

Following the procedure of Example 5 and substituting the appropriate starting materials, compounds and reagents, the following Compounds of the invention were also prepared:

| Cpd | $R_{10}$ | MS m/e ($MH^+$). |
|---|---|---|
| 37 | naphthalene-2-yl-acetyl | 657 |
| 38 | 2-naphthoyl | 641 ($MH^-$) |
| 39 | 1-(4-hydroxyphenyl) | 581 |
| 40 | 1-(4-methoxyphenyl) | 595 |
| 41 | N-[5-(sulfonyl)-thiophene-2-ylmethyl]-benzamide | 768 |
| 42 | 6-chloro-5-sulfonyl-imidazo[2,1-b]thiazole | 709 |
| 43 | Naphthyl-2-aminocarbonyl | 658 |
| 44 | 1-(4-fluorophenyl) | 583 |

BIOLOGICAL EXPERIMENTAL EXAMPLES

The utility of the compounds of the present invention as a serine protease inhibitor and, particularly, as a cathepsin G or chymase inhibitor useful for the treatment of inflammatory or serine protease mediated disorders can be determined according to the procedures described herein.

Example 1

Enzyme-Catalyzed Hydrolysis Assays

Cathepsin G

Enzyme-catalyzed hydrolysis rates were measured spectrophotometrically using human neutrophil cathepsin G (Athens Research and Technology) or human skin chymase (Cortex Biochem), a chromogenic substrate (Suc-Ala-Ala- Pro-Phe-pNa) (Bachem) in aqueous buffer (100 mM Hepes, 500 mM NaCl, pH 7.4 for catG; 450 mM Tris, 1800 mM NaCl, pH 8.0 for chymase), and a microplate reader (Molecular Devices). $IC_{50}$ experiments were conducted by fixing the enzyme and substrate concentrations (70 nM enzyme, 5 mM substrate for cat G, 10 nM enzyme, 0.7 mM substrate for chymase) and varying the inhibitor concentration. Changes in absorbance at 405 nM were monitored using the software program Softmax (Molecular Devices), upon addition of enzyme, with and without inhibitor present at 37° C. for 30 minutes. Percent inhibition was calculated by comparing the initial reaction slopes of the samples without inhibitor to those with inhibitor. $IC_{50}$ values were determined using a four parameter fit logistics model. The term "NT" indicates a compound that was not tested.

Table 4 summarizes the assay results for cathepsin G and chymase inhibition for compounds of the present invention:

TABLE 4

| Cpd | $IC_{50}$ (μM) CatG | n | $IC_{50}$ (μM) Chymase | n |
|---|---|---|---|---|
| 1 | 0.083 ± 0.014 | 7 | 0.0053 ± 0.0019 | 8 |
| 2 | 0.081 ± 0.009 | 70 | 0.0067 ± 0.0018 | 70 |
| 3 | 0.068 ± 0.019 | 2 | 0.072 ± 0.008 | 3 |
| 4 | 0.090 ± 0.020 | 5 | 0.0039 ± 0.0001 | 4 |
| 5 | 0.072 ± 0.021 | 5 | 0.2 ± 0.4 | 6 |
| 6 | 0.067 ± 0.014 | 4 | 0.0035 ± 0.0015 | 2 |
| 7 | 0.210 ± 0.050 | 12 | 0.008 ± 0.022 | 1 |
| 8 | 0.130 ± 0.010 | 11 | 0.0074 ± 0.0022 | 8 |
| 9 | 0.053 ± 0.015 | 5 | 0.011 ± 0.003 | 2 |
| 10 | 0.053 ± 0.016 | 5 | 0.014 ± 0.006 | 5 |
| 11 | 4.9 ± 2.8 | 2 | 0.032 | 1 |
| 12 | 0.179 ± 0.038 | 10 | 0.0073 ± 0.0017 | 10 |
| 13 | 0.064 ± 0.008 | 3 | 0.004 | 1 |
| 14 | 0.230 ± 0.030 | 6 | 0.010 ± 0.001 | 9 |
| 15 | 0.075 ± 0.030 | 5 | 0.017 ± 0.005 | 3 |
| 16 | 0.190 ± 0.020 | 7 | 0.0085 ± 0.0023 | 7 |
| 17 | 0.098 ± 0.026 | 4 | 0.0072 ± 0.0015 | 6 |
| 18 | 0.028 ± 0.006 | 3 | 0.0010 | 1 |
| 19 | 0.238 ± 0.030 | 8 | 0.022 ± 0.062 | 9 |
| 20 | 0.090 ± 0.023 | 5 | 0.004 ± 0.002 | 2 |
| 21 | 0.070 ± 0.020 | 5 | 0.0096 ± 0.0034 | 5 |
| 22 | 0.140 ± 0.040 | 18 | 0.009 ± 0.023 | 12 |
| 23 | 0.670 | 1 | 0.416 | 1 |
| 24 | 0.078 ± 0.015 | 7 | 0.0035 ± 0.0013 | 6 |
| 25 | 0.156 ± 0.028 | 7 | 0.0097 ± 0.0035 | 7 |
| 26 | 0.096 ± 0.018 | 3 | 0.015 ± 0.001 | 3 |
| 27 | 0.070 ± 0.010 | 4 | 0.0051 ± 0.0022 | 4 |
| 28 | 0.400 ± 0.090 | 11 | 0.036 ± 0.011 | 10 |
| 29 | 0.150 ± 0.030 | 13 | 0.0082 ± 0.0028 | 10 |
| 30 | 0.590 ± 0.040 | 2 | 0.0158 ± 0.0008 | 2 |
| 31 | >100.0 | 1 | 14.95 ± 0.67 | 2 |
| 32 | 0.86 ± 0.03 | 2 | 0.31 | 1 |
| 33 | 0.121 ± 0.007 | 2 | 0.001 ± 0.000 | 2 |
| 34 | 0.09 ± 0.04 | 3 | 0.007 ± 0.001 | 2 |

TABLE 4-continued

| Cpd | $IC_{50}$ (μM) CatG | n | $IC_{50}$ (μM) Chymase | n |
|---|---|---|---|---|
| 35 | 0.56 ± 0.18 | 3 | | |
| 37 | 0.74 ± 0.29 | 3 | | |
| 38 | 0.78 ± 0.22 | 2 | | |
| 39 | 0.18 ± 0.05 | 2 | | |
| 40 | 0.17 ± 0.05 | 2 | | |
| 41 | 0.31 | 1 | | |
| 42 | 0.14 ± 0.03 | 2 | | |
| 43 | 0.95 ± 0.21 | 5 | | |
| 44 | 0.52 ± 0.29 | 2 | | |

Example 2

Anti-Asthmatic Effects in a Sheep Model of Asthma

The efficacy of Compound 2 for the treatment of asthma was evaluated in a validated model of *Ascaris suum* antigen-induced asthmatic response in conscious sheep (Abraham, W. M., Pharmacology of allergen-induced early and late airway responses and antigen-induced airway hyperresponsiveness in allergic sheep, *Pulmonary Pharmacology*, 1989, 2, 33-40).

Experimental Protocol

Baseline dose response curves to aerosol carbachol were obtained 1-3 days prior to antigen challenge. Baseline values of specific lung resistance ($SR_L$) were obtained and the sheep were then given a specified amount (mg) of the test compound as an inhaled aerosol at a specified time before antigen challenge. Post drug measurements of $SR_L$ were obtained and the sheep were then challenged with *Ascaris suum* antigen. Measurements of $SR_L$ were obtained immediately after challenge, hourly from 1-6 h after challenge and on the half-hour from 6½-8 h after challenge. Measurements of $SR_L$ were obtained 24 h after challenge followed by a 24 h post-challenge with carbachol to measure airway hyperreactivity.

Compound 2 was administered as an aerosol at 0.1 mg/Kg/dose, twice-a-day (BID) for three consecutive days, followed by a dose on day 4, 0.5 h prior to antigen challenge. *Ascaris suum* antigen challenge was given at the zero time point.

FIG. 1 shows that the early airway response (0-2 h after antigen challenge) was dramatically reduced and that the late airway response (6-8 h after antigen challenge) was completely blocked (n=4 sheep/group).

Figure 2:
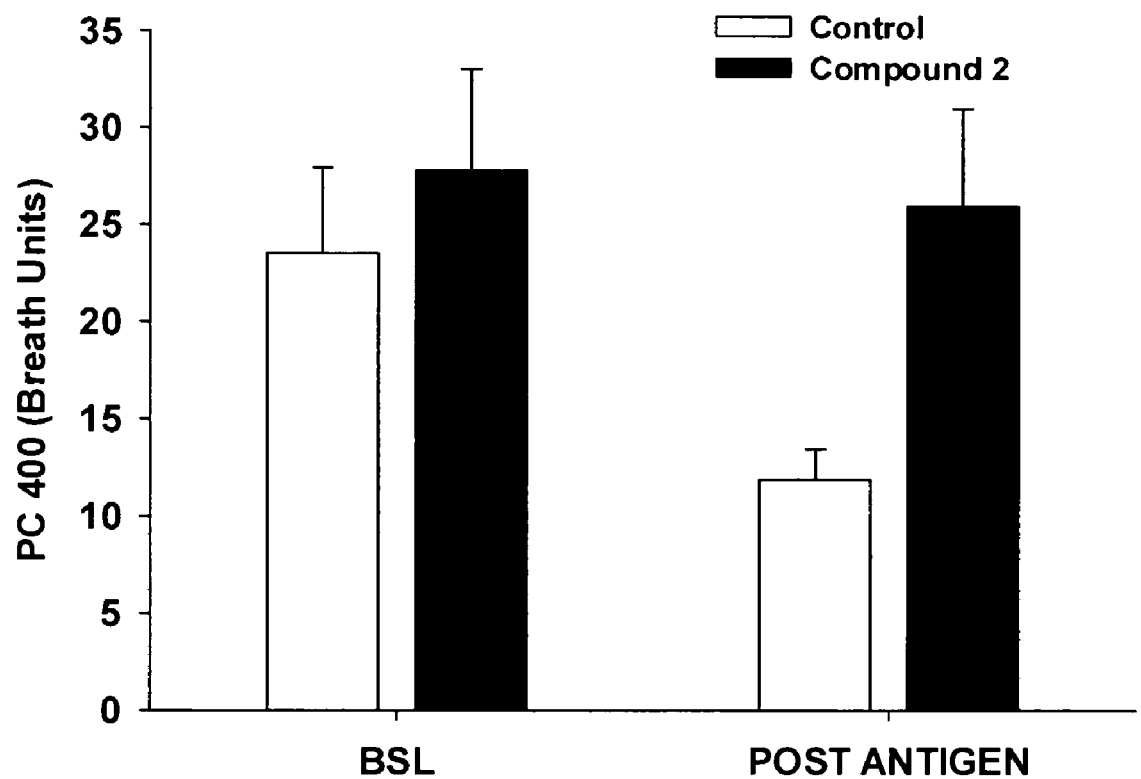
FIG. 2 shows the change in the cumulative carbachol dose required to increase $SR_L$ 400% (PC 400) from a baseline value (BSL) measured at 24 hours post-dosing of Compound 2 in the spontaneous *ascaris suum* antigen-induced model of asthma in sheep compared to a 24 hour post-dosing challenge with carbachol (Post Antigen).

FIG. 2 shows that the delayed airway hyperreactivity measured at 24 h post antigen challenge as measured using carbachol challenge was also completely blocked.

In addition to blocking the increase in airway resistance, as shown in Table 5, Compound 2 also blocked the rise in inflammatory cell numbers in the broncho-alveolar lavage (BAL) fluid sampled from these sheep.

TABLE 5

| Treatment Group/Time | BAL Cell Count (×1000/mL) | | | |
|---|---|---|---|---|
| Baseline | Neutrophils | Lymphocytes | Eosinophils | Macrophages |
| Baseline | 22.04 ± 12.89 | 4.82 ± 1.74 | 6.29 ± 3.98 | 172.2 ± 20.8 |
| 8 h Post Antigen | 24.55 ± 14.08 | 13.39 ± 5.44 | 61.58 ± 29.87 | 209.3 ± 44.7 |
| 24 h Post Antigen | 111.7 ± 38.9 | 36.30 ± 15.68 | 168.4 ± 95.1 | 245.6 ± 20.4 |
| Compound 2 (1.0 mg/kg × 4 days) (last dose - 30 min prior to antigen challenge) | | | | |
| Baseline | 12.66 ± 2.07 | 3.15 ± 0.79 | 0.00 | 69.06 ± 1.97 |
| 8 h Post Antigen | 3.17 ± 0.65 | 4.16 ± 1.10 | 0.37 ± 0.32 | 77.85 ± 2.36 |
| 24 h Post Antigen | 3.86 ± 0.95 | 3.72 ± 0.77 | 0.04 ± 0.03 | 75.16 ± 2.71 |

What is claimed is:

1. A compound of Formula (Ib):

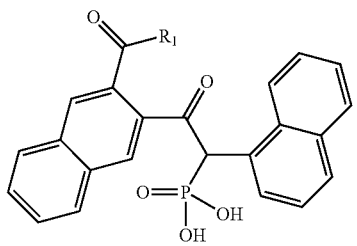

Formula (Ib)

wherein

R₁ is a piperidine ring (wherein the point of attachment for the heterocyclyl ring at R₁ is a nitrogen ring atom); wherein the piperidine ring is optionally substituted with one to two aryl substituents:

and, wherein the aryl substituent is optionally substituted with one to four substituents independently selected from the group consisting of $C_{1-4}$ alkyl, $C_{2-4}$ alkenyl, $C_{1-4}$ alkoxy, cycloalkyl, heterocyclyl, aryl, aryl($C_{1-4}$ alkyl, aryloxy, heteroaryl, heteroaryl($C_{1-4}$alkyl, halogen, hydroxy, nitro, (halo)$_{1-3}$($C_{1-4}$alkyl and (halo)$_{1-3}$($C_{1-4}$alkoxy;

and racemates, enantiomers, diastereomers and salts thereof.

2. The compound of claim 1 wherein R₁ is a piperidine ring (wherein the point of attachment for the piperidine ring at R₁ is a nitrogen ring atom) optionally substituted with an aryl substituent; and, wherein the aryl substituent is optionally substituted with one to two substituents independently selected from the group consisting of $C_{1-4}$ alkyl, $C_{1-4}$ alkoxy, aryl, heteroaryl, halogen, hydroxy, (halo)$_{1-3}$($C_{1-4}$)alkyl and (halo)$_{1-3}$($C_{1-4}$)alkoxy.

3. The compound of claim 1 wherein R₁ is a piperidine (wherein the point of attachment for the piperidine at R₁ is a nitrogen ring atom) optionally substituted with an aryl substituent; and, wherein the aryl substituent is optionally substituted with one to two substituents independently selected from the group consisting of $C_{1-4}$ alkoxy and aryl.

4. The compound of claim 1 wherein the compound of Formula (Ib) is selected from the group consisting of:

[1-(1-Naphthalenyl)-2-oxo-2-[3-[(4-phenyl-1-piperidinyl)carbonyl]-2-naphthalenyl]ethyl]-phosphonic acid;

[2-[3-[[4-(4-Methoxyphenyl)-1-piperidinyl]carbonyl]-2-naphthalenyl]-1-(1-naphthalenyl)-2-oxoethyl]-phosphonic acid; and

[2-[3-[[4-(3-Methoxyphenyl)-1-piperidinyl]carbonyl]-2-naphthalenyl]-1-(1-naphthalenyl)-2-oxoethyl]-phosphonic acid.

5. The compound of claim 1 wherein the compound of Formula (Ib) is contacted with a pharmaceutically acceptable cation to form a salt.

6. The compound of claim 5 wherein the cation is selected from the group consisting of aluminum, ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH₃, NH₄OH, N-methyl-D-glucamine, piperidine, potassium, potassium-t-butoxide, potassium hydroxide (aqueous), procaine, quinine, SEH, sodium, sodium carbonate, sodium-2-ethylhexanoate, sodium hydroxide, triethanolamine, tromethane and zinc.

7. The compound of claim 6 wherein the cation is selected from benzathine, t-butylamine, calcium gluconate, calcium hydroxide, choline bicarbonate, choline chloride, cyclohexylamine, diethanolamine, ethylenediamine, LiOMe, L-lysine, NH₃, NH₄OH, N-methyl-D-glucamine, piperidine, potassium-t-butoxide, potassium hydroxide (aqueous), procaine, quinine, sodium carbonate, sodium-2-ethylhexanoate, sodium hydroxide, triethanolamine and tromethane.

8. The compound of claim 7 wherein the cation is selected from t-butylamine, NH₄OH and tromethane.

9. The compound of claim 8 wherein the cation is tromethane.

* * * * *